US009309500B2

(12) United States Patent
Klee et al.

(10) Patent No.: US 9,309,500 B2
(45) Date of Patent: Apr. 12, 2016

(54) **TOMATO CATECHOL-*O*-METHYLTRANSFERASE SEQUENCES AND METHODS OF USE**

(71) Applicant: University of Florida Research Foundation, Inc., Gainesville, FL (US)

(72) Inventors: Harry J. Klee, Gainesville, FL (US); Denise Marie Tieman, Gainesville, FL (US); Melissa Hamner Mageroy, Vancouver (CA)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 691 days.

(21) Appl. No.: 13/622,668

(22) Filed: Sep. 19, 2012

(65) Prior Publication Data

US 2013/0074216 A1  Mar. 21, 2013

Related U.S. Application Data

(60) Provisional application No. 61/536,690, filed on Sep. 20, 2011.

(51) Int. Cl.
*A01H 5/00* (2006.01)
*C12N 9/10* (2006.01)
*C12N 15/82* (2006.01)
(52) U.S. Cl.
CPC .......... *C12N 9/1011* (2013.01); *C12N 15/8243* (2013.01)

(58) Field of Classification Search
CPC .................................. A01H 5/00; C12N 15/82
See application file for complete search history.

(56) References Cited

U.S. PATENT DOCUMENTS

| 2003/0101478 | A1 | 5/2003 | Perera et al. | |
|---|---|---|---|---|
| 2008/0148432 | A1* | 6/2008 | Abad | 800/279 |
| 2009/0313728 | A1* | 12/2009 | Lepelley et al. | 800/307 |

FOREIGN PATENT DOCUMENTS

| KR | 2011023949 | 5/2010 |
|---|---|---|
| WO | 0134817 A2 | 5/2001 |
| WO | 03046163 A2 | 6/2003 |
| WO | WO03046163 | 6/2003 |

OTHER PUBLICATIONS

Mageroy, Malissa H: "A solanum lycopersicum catechol-0-methyltransferase implicated in the synthesis of the flavour molecule guaiacol", Plant Biology 2011: Saturday, Aug. 6-Wednesday Aug. 10, 2011—Minneapolis, Minnesota.
Supplemental Search Report and Opinion for application No. EP 12 83 4126; Apr. 1, 2015; Munich; 7 pages.

(Continued)

*Primary Examiner* — Russell Kallis
*Assistant Examiner* — Weihua Weihua
(74) *Attorney, Agent, or Firm* — Thomas Horstemeyer LLC

(57) ABSTRACT

The present disclosure provides isolated DNA molecules encoding tomato O-methyltransferases (OMT); tomato OMT proteins; OMT antisense molecules; vectors, plant cells and plants including tomato OMT DNA molecules or OMT antisense molecules; genetic markers for tomato OMT genes; and methods of increasing or decreasing the amount of guaiacol produced by a plant.

14 Claims, 27 Drawing Sheets

(56) References Cited

OTHER PUBLICATIONS

DATABASE UniProt [Online] Nov. 1, 1996, SubName: Fuii=Catechol 0-methyltransferase {ECO:00003131 EMBL:CAA50561.1}; EC=2.1.1.6 {ECO:00003131 EMBL:CAA50561.1); DGASMGPLLA LLQDKVFINS WFELKDAVLE GGVPFDRVHG VVHAFEYPKS DPKFNDVFNK XP002737626, retrieved from EBI accession No. UNIPROT:Unreviewed Database accession No. Unreviewed; 1 page.
Maury, S., Geoffroy, P. and Legrand, M. (1999) Tobacco O-methyltransferases involved in phenylpropanoid metabolism.the different caffeoyl-coenzyme A/5-hydroxyferuloyl-coenzyme a 3/5-O-methyltransferase and caffeic Acid/5-hydroxyferulic acid 3/5-O-methyltransferase classes have distinct substrate specificities and expression patterns. Plant Physiology, 121(1), 215-224.
McCormick, S., Niedermeyer, J., Fry, J., Barnason, A., Horsch, R. and Fraley, R. (1986) Leaf disc transformation of cultivated tomato (*L. esculentum*) using agrobacterium tumefaciens. Plant Cell Reports, 5(2), 81-84.
Morse, A.M., Tschaplinski, T. J., Dervinis, C., Pijut, P. M., Schmelz, E. A., Day, W. and Davis, J. M. (2007) Salicylate and catechol levels are maintained in nahG transgenic poplar. Phytochemistry, 68(15), 2043-2052.
Pellegrini, L., Geoffroy, P., Fritig, B. and Legrand, M. (1993) Molecular cloning and expression of a new class of ortho-diphenol-O-methyltransferases induced in tobacco (*nicotianatabacum* L.) leaves by infection or elicitor treatment. Plant Physiology, 103(2), 509-517.
Richins, R.D., Scholthof, H. B. and Shepherd, R. J. (1987) Sequence of figwort mosaic virus DNA (caulimovirus group). Nucleic Acids Research, 15(20), 8451-8466.
Serra Bonveh, J. and Ventura Coll, F. (1998) Evaluation of smoky taste in cocoa powder.J. Agric. Food Chem., 46(2), 620-624.
Wang, J. and Pichersky, E. (1999) Identification of specific residues involved in substrate discrimination in two plant O-methyltransferases. Arch. Biochem. Biophys.,368(1), 172-180.
Van Wees, S.C.M. and Glazebrook, J. (2003) Loss of non-host resistance of arabidopsisNahG to pseudomonas syringaepv. phaseolicola is due to degradation products of salicylic acid. The Plant Journal, 33(4), 733-742.
Zanor, M.I., Rambla, J., Chap, J., Steppa, A., Medina, A., Granell, A., Fernie, A. R. and Causse, M. (2009) Metabolic characterization of loci affecting sensory attributes in tomato allows an assessment of the influence of the levels of primary metabolites and volatile organic contents. Journal of Experimental Botany, 60(7), 2139-2154.
Zierler, B., Siegmund, B. and Pfannhauser, W. (2004) Determination of off-flavour compounds in apple juice caused by microorganisms using headspace solid phase microextraction—gas chromatography—mass spectrometry.Anal.Chim. Acta, 520(1-2), 3-11.
Guillen, M.D., Manzanos, M. J. and Zabala, L. (1995) Study of a commercial liquid smoke flavoring by means of gas Chromatography/Mass spectrometry and fourier transform infrared spectroscopy. J. Agric. Food Chem., 43(2), 463-468.
Karimi, M., Inzé, D. and Depicker, A. (2002) GATEWAY(TM) vectors for agrobacterium-mediated plant transformation. Trends Plant Sci., 7(5), 193-195.
Kumazawa, K. and Masuda, H. (2002) Identification of potent odorants in different green tea varieties using flavor dilution technique. J. Agric. Food Chem., 50(20), 5660-5663.
Lam, K., Ibrahim, R., Behdad, B. and Dayanandana, S. (2007) Structure, function, and evolution of plant O-methyltransferases. Genome, 50(11), 1001-1013.
Gang, D.R. (2005) Evolution of Flavors and Scents.Annu. Rev. Plant Biol., 56(1), 301-325.
Bai, Y. and Lindhout, P. (2007) Domestication and breeding of tomatoes: What have we gained and what can we gain in the future? Annals of Botany, 100(5), 1085-1094.
Brading, P.A., Hammond-Kosack, K. E., Parr, A. and Jones, J. D. G. (2000) Salicylic acid is not required for cf-2- and cf-9-dependent resistance of tomato to cladosporiumfulvum. The Plant Journal, 23(3), 305-318.
Dorfner, R., Ferge, T., Kettrup, A., Zimmermann, R. and Yeretzian, C. (2003) Real-time monitoring of 4-vinylguaiacol, guaiacol, and phenol during coffee roasting by resonant laser ionization time-of-flight mass spectrometry.J. Agric. Food Chem., 51(19), 5768-5773.
Friedrich, L, Vernooij, B., Gaffney, T., Morse, A. and Ryals, J. (1995) Characterization of tobacco plants expressing a bacterial salicylate hydroxylase gene.Plant Molecular Biology, 29(5), 959-968.
Gang, D.R., Lavid, N., Zubieta, C., Chen, F., Beuerle, T., Lewinsohn, E., Noel, J. P. and Pichersky, E. (2002) Characterization of phenylpropene O-methyltransferases from sweet basil: Facile change of substrate specificity and convergent evolution within a plant O-methyltransferase family.The Plant Cell Online, 14(2), 505-519.
Gaffney, T., Friedrich, L, Vernooij, B., Negrotto, D., Nye, G., Uknes, S., Ward, E., Kessmann, H. and Ryals, J. (1993) Requirement of salicylic acid for the induction of systemic acquired resistance.Science, 261(5122), 754-756.
Rodriguez, M.L., Belloch, C., Villa, M., Uruburu, F., Larriba, G. and Coque, J. R. (2003) Degradation of vanillic acid and production of guaiacol by microorganisms isolated from cork samples. FEMS Microbiol.Lett.,220(1), 49-55.
Hayasaka, Y., Baldock, G. A., Pardon, K. H., Jeffery, D. W. and Herderich, M. J. (2010) Investigation into the formation of guaiacol conjugates in berries and leaves of grapevine vitisvinifera L. cv. cabernet sauvignon using stable isotope tracers combined with HPLC-MS and MS/MS analysis. J. Agric. Food Chem., 58(4), 2076-2081.
The International Search Report and Written Opinion dated Mar. 28, 2013.
Mageroy, et al., "A Solanum Lycopersicum Catechol-O-Methyltransferase Involved in Synthesis of the Flavor Molecule Guaiacol," The Plant Journal, Dec. 23, 2011, vol. 69, Issue 6, pp. 1043-1051.

\* cited by examiner 1) 
2) 
3)

| SUBSTRATE | S1OMT1 RELATIVE ACTIVITY |
|---|---|
| CATECHOL | 100% |
| GUAIACOL | 0% |
| SALICYLIC ACID | 0% |
| BENZOIC ACID | 0% |
| ORICINOL | 9% |
| CAFFEIC ACID | 2% |

4) 
5) 
6)

| | $K_m(\mu M)$ | $K_{cat}(s^{-1})$ |
|---|---|---|
| S1OMT1 | 8.36 ± 1.78 | 9.67 ± 2.42 |

|  | GUAIACOL EMITTED nM disc$^{-1}$hr$^{-1}$ | |
|---|---|---|
|  | CONTROL | CATECHOL |
| FLORA-DADE | 0.0132 | 0.4755 |
| S1OMT1$_{OE}$ | 0.0580 | 3.0278 |

FIG. 7

S. lycopersicum: SEQ ID NO: 3

S. Pennellii: SEQ ID NO: 4

```
s.lycopersicum  MGSTANIQLATQSEDEERNCTYAMQLLSSSVLPFVLHSTIQLDVFDILAKDKAATKLSAL
s.pennellii     MGSTANIQLPTQSENEERNCTYAMQLLSSSVLPFVLHSTIQLDVFEILAKDKAATKLSAL
                ******* *:******************************:*********** s.lycopersicum  EIVSHMPNCKNPDAATMLDRMLYVLASYSLLDCSVVEEGNGVTERRYGLSRVGKFFVRDE
s.pennellii     EIVSHMPNCKNPDAATMLDRMLYVLASYSLLDCTVVEEGNGVTERRYGLSRVGKFFVRDE
                *******************************:************************ s.lycopersicum  DGASMGPLLALLQDKVFINSWFELKDAVLEGGVPFDRVHGVHAFEYPKLDPKFNDVFNQA
s.pennellii     DGASMGPLLALLQDKAFINSWFELKDAVLEGGVPFDRVHGVHAFEYPKLDPKFNDVFNQA
                *************.****************************************** s.lycopersicum  MINHTTVVMKRILENYKGFENLKTLVDGGGLGVNLKMITSKYPTIKGTNFDLPHVVQHA
s.pennellii     MINHTTVVMKRILENYKGFENLKTLVDGGGLGVNLKMITSKYPTIKGTNFDLPHVVQHA
                *********************************************************** s.lycopersicum  PSYPGVDHVGGDMFESVPQGDAIFMKWILHDWSDGHCLKLLKNCHKALPDNGKVIVVEAN
s.pennellii     TSYPGVDHVGGDMFESVPQGDAIFMKWILHDWSDGHCLKLLKNCHKALPDNGKVIVVEAN
                .*********************************************************** s.lycopersicum  LPVKPDTDTTVVGVSQCDLIMMAQNPGGKERSEQEFRALASEAGFKGVNLICCVCNFWVM
s.pennellii     LPVKPDTDTTVVGVSQCDLIMMAQNPGGKERSEQEFRALASEAGFKGVNLICCVCNFWVM
                ************************************************************ s.lycopersicum  EFYK
s.pennellii     EFYK
                ****
```

FIG. 8A

M82 and Heinz 1706: SEQ ID NO: 5
S. pennellii: SEQ ID NO: 6

```
M82          TATATATCAATTTTCAACATGATA------TAAAGATAGGCATTTGGAGAGAAATTTG
Heinz1706    TATATATCAATTTTCAACATGATA------TAAAGATAGGCATTTGGAGAGAAATTTG
S.pennellii  TATATATCAATTTTCAACATAAGAATTCAGATAAAGATAGGCATTTGGAGAGAAATTTG
             ********************    *     ******************************

M82          ATAAAACCCGATGTTGTACAAATTTTAAGGGGTTTAGTTGTAGAATATGAAATACTAGTA
Heinz1706    ATAAAACCCGATGTTGTACAAATTTTAAGGGGTTTAGTTGTAGAATATGAAATACTAGTA
S.pennellii  ATAAAACCCGATTTGTACAAATTTTAAGGG-TTCAGTTATAGCATATGAAATACTAGTA
             ************  ***************** ** ***** *** ***************

M82          ATCTGTAGCATGAAATAAGAAGGCATATAGGTATCGGGTGGCATTATTTTATGAGCCCAC
Heinz1706    ATCTGTAGCATGAAATAAGAAGGCATATAGGTATCGGGTGGCATTATTTTATGAGCCCAC
S.pennellii  ATCTGTAGCATGAAATAAGAAGGCATATAGGTATCGGGTGGCCATTATTTTATGAGCCCAC
             ****************************************** *****************

M82          TTAGCCATTAACTTTCAAAATAAAATGAACATACTTGGGCCAGAACTCAGCGAATATGG
Heinz1706    TTAGCCATTAACTTTCAAAATAAAATGAACATACTTGGGCCAGAACTCAGCGAATATGG
S.pennellii  TTAGCCATTAA----------AAATGAACATAATTGGGCCAGACCTCAGCGAATATGG
             ***********          *********** ********** ****************

M82          GCTTAGCAATTGCATATGGACCTCACTGT---------TAGGTTCCCTATATAACTAG
Heinz1706    GCTTAGCAATTGCATATGGACCTCACTGT---------TAGGTTCCCTATATAACTAG
S.pennellii  GCTTAATAATTGCATATGGACCTCACTTACTGTGCAACTTATGCTAGGTTCCCTATATAACTAG
             *****  ******************** ******    ************************

M82          TTCACATAATACTTATTGTTACAAGGAGCTGAATTTGTAACAAGGTCATATATATATA
Heinz1706    TTCACATAATACTTATTGTTACAAGGAGCTGAATTTGTAACAAGGTCATATATATATA
S.pennellii  TTCACATAATACTTTTGTTACAAGGAGCTGAATTTGTAACAAGGTCATATATATATATA--
             ************** ************************************************
```

FIG. 8B

M82 and Heinz 1706: SEQ ID NO: 5

S. pennellii: SEQ ID NO: 6

```
M82         TATACTGTACTAACATTATAAAGATAAGCGTGCAAAAACCAATAAACGAATAATGGTTAC
Heinz1706   TATACTGTACTAACATTATAAAGATAAGCGTGCAAAAACCAATAAACGAATAATGGTTAC
S.pennellii --CACTGTACTAACATTATAAAGATAAGCGTGCAAAAACCAACAAACGATAATGGTTAC
              ********************************** ****** *************

M82         TTCGGATTAAGTCAAGGAAATACTGAAATCAAGGAGTTTGATTTTAAGAAAGAACTTTAC
Heinz1706   TTCGGATTAAGTCAAGGAAATACTGAAATCAAGGAGTTTGATTTTAAGAAAGAACTTTAC
S.pennellii TTCGGATTAAGTCCAGGAAATACTAAAATCAAGGAGTTTGATTTTAAGAAAGAACTTTAC
            ************* ********* ************************************

M82         TTGATGTAGAATTTTAAATCAAGAGAGTTTGAGT---------------------------
Heinz1706   TTGATGTAGAATTTTAAATCAAGAGAGTTTGAGT---------------------------
S.pennellii TTTATGTAGAATTTTAAATCAAGAGAGTTTGAGTTGAGGTGAGTTTGAAGTGAAAGAA
            ** ******************************

M82         -AACACTCTGAAGAGTGTGCTTGAGAGTCACTCAGAACAAGGTGTGCACTCACAGAGCA
Heinz1706   -AACACTCTGAAGAGTGTGCTTGAGAGTCACTCAGAACAAGGTGTGCACTCACAGAGCA
S.pennellii TAACTCTCTAAAGAGTTGTGCTTGAGAGTCACTCAGAACAAGGTGTGCACTCACAGAGCA
             *** ***** ***** *******************************************

M82         AAAACCAATTGGCTTCGCGCCAATGTTGTTTGACTATTGAAGGAACACATTGAAGAATCAGG
Heinz1706   AAAACCAATTGGCTTCGCGCCAATGTTGTTTGACTATTGAAGGAACACATTGAAGAATCAGG
S.pennellii AAAACCAATTGGCTTCGCGCCAATGTTGTTTGACTATTGAAGGAACACATTGAAGAATCAGG
            ************************************************************

M82         TCCTAATGCAACTACAAGTTTTAGCCTTCATGTGTTCATTTGAGTTGTAATATTAATGCA
Heinz1706   TCCTAATGCAACTACAAGTTTTAGCCTTCATGTGTTCATTTGAGTTGTAATATTAATGCA
S.pennellii TCCTAATGCAACTACAAGTTTTAGCGTTCATGTGTTCATG-GAGTTGTAATATTAATGCA
            ************************* ************* *******************
```

FIG. 8C

M82 and Heinz 1706: SEQ ID NO: 5
S. pennellii: SEQ ID NO: 6

```
M82          AATCTTAATTTTTAGTGTGTTATTGGATTATATAATCTTCAAGTTGGGATAACTTAAAGATTT
Heinz1706    AATCTTAATTTTTAGTGTGTTATTGGATTATATAATCTTCAAGTTGGGATAACTTAAAGATTT
S.pennellii  A-TCTTAATTCTTGTGTGTTATTGGATTATATAATCTTCAAGTTGGGATAACTTAAAGATTT
             * ********* *  ***********************************************

M82          GAGGACATATATCTTGAGAGGTTTGTGAGTTGTTAAGAATTAGAGTTCATAATTTGTGG
Heinz1706    GAGGACATATATCTTGAGAGGTTTGTGAGTTGTTAAGAATTAGAGTTCATAATTTGTGG
S.pennellii  GAGGACATATATCTTGAGAGGTTTGTGAGTTGTTAAGAATTAGAGTTCATAATTTTGTGG
             ******************************************************* ****

M82          TTTAGAATTGTGTTAAGAATTAGAGTTCATAATGTCTCTTGTTGAAAGGCTCATTGTGCTTTAG
Heinz1706    TTTAGAATTGTGTTAAGAATTAGAGTTCATAATGTCTCTTGTTGAAAGGCTCATTGTGCTTTAG
S.pennellii  ATTACA------------TAGA--TTCATAAATGTCTCTGTTGTTGAAAGGCTCATTGTGGATTAG
             *** *              ****  ****** ****** ****** *************   ****

M82          AAAAGTTGTGGTTAAATGTTGTAGATGTACATGTGATTTTT----------GTGAACTGGA
Heinz1706    AAAAGTTGTGGTTAAATGTTGTAGATGTACATGTGATTTTT----------GTGAACTGGA
S.pennellii  AAAAGTTGTGGTTAAATGTTGTAGATGTACATGTGATTTTTATGACTTTTGTGAGCTGGA
             *****************************************          **** *****

M82          TATTTTTACATAAAATAATGTAGTGTTGATACCATTTTGTTAAAGCACATTAGCCAAGA
Heinz1706    TATTTTTACATAAAAATAATGTAGTGTTGATACCATTTTGTTAAAGCACATTAGCCAAGA
S.pennellii  TATTTTTACATAAAAATAATGTAGTGTTTATCTATCTTGTTAAAGCACATTAGCCAAGA
             ************** ************* **  *  *********************

M82          TACTAGTTAATGGGACTATAAGTAGCGTCACGAAATTCTTTTGGTGAATTCGGTTTAGA
Heinz1706    TACTAGTTAATGGGACTATAAGTAGCGTCACGAAATTCTTTTGGTGAATTCGGTTTAGA
S.pennellii  TACTAGTTAATGGGACTATAAGTAGCGTCACGAAATTCTTTTGGTGAATTCGGTTTAGA
             ************************************************************
```

FIG. 8D

M82 and Heinz 1706: SEQ ID NO: 5
S. pennellii: SEQ ID NO: 6

```
M82          ATTAATAGAAGTTTAGCATTAATAATAGGATTATTTCAAGTGACAAGAGAATCATTCAAAAATG
Heinz1706    ATTAATAGAAGTTTAGCATTAATAATAGGATTATTTCAAGTGACAAGAGAATCATTCAAAAATG
S.pennellii  ATTAATAGAAGTTTAGCATTAATAATAGGATTATTTAGAGTAACAAGAGAATCATTCAAAAATG
             ************************************  *** ********************

M82          GTAAACATCACTTACTTAGGAAGCTAAAAGAAAAACCTTTAAAGTAGGTTATCTTTTCCATCT
Heinz1706    GTAAACATCACTTACTTAGGAAGCTAAAAGAAAAACCTTTAAAGTAGGTTATCTTTTCCATCT
S.pennellii  GTAAACATCACTTACTTAGGAAGCTAAAAGAAAAACCTTTAAAGTAGGTTAGGT-ATCTTTCCATCT
             **************************************************   * ******** ****

M82          AGAAAGTGATTGAAAAAATAAATCTAGTAATGTTAGGTGCAACAACTTTAAATCATCACA
Heinz1706    AGAAAGTGATTGAAAAAATAAATCTAGTAATGTTAGGTGCAACAACTTTAAATCATCACA
S.pennellii  AGAAAGTGATTGAAAAA-CAAATCTAGTAATGTTAGGTGCAACAACTTTGAATCATCACA
             *****************  ****************************** **********

M82          GAGAAAAAGTGGACTGAAAAAGAATAATCATAAAGGAGATTTCATGATTTGATATATACA
Heinz1706    GAGAAAAAGTGGACTGAAAAAGAATAATCATAAAGGAGATTTCATGATTTGATATATACA
S.pennellii  AAGAAAAAGTGGACTGAAAAAGAATAATCATAAAGGAGATTTCATGATTTGATATATACA
              ***********************************************************

M82          TACATAT------------------TTATTTTTTGTTATACCAAACAAAGATTTTATT
Heinz1706    TACATAT------------------TTATTTTTTATTTTGTTATACCAAACAAAGATTTTATT
S.pennellii  TATATATACATACATATTTATTTATTTATTTTTATTTTGTTATACCAAACAAAGATTTTATT
             ** ****                                       ****************

M82          TATTTATTGTTTTTAAAAAAAAAGAAAAAATCTCTAGTTGAAGACTCTTTCTTGCAAATTTC
Heinz1706    TATTTATTGTTTTTAAAAAAAAAGAAAAAATCTCTAGTTGAAGACTCTTTCTTGCAAATTTC
S.pennellii  TATTTATTGTTTTTAAAATGAAGAAAAAATGAAGAAAAAATCTCTAGTTGAAGACTCTTTCTTGCAAATTTC
             ******************   ************************************
```

FIG. 8E

M82 and Heinz 1706: SEQ ID NO: 5
S. pennellii: SEQ ID NO: 6

```
M82         AACAAGCAACGTATCAAGGTAAAAAAAAAAAAAATAACACATGTAATGTATCTTCATATGT
Heinz1706   AACAAGCAACGTATCAAGGTAAAAAAAAAAAAAATAACACATGTAATGTATCTTCATATGT
S.pennellii AACAAGTAACTTATCAAGGTAAAAAAAA-----TAACACATGTAATGTATCTTCATATGT
            ****** *** *****************     ***************************

M82         CATCATTAAATAGAAGGGGTTAGTTAGAATTTAGTAATACATTCAAAAAAACTAACAGC
Heinz1706   CATCATTAAATAGAAGGGGTTAGTTAGAATTTAGTAATACATTCAAAAAAACTAACAGC
S.pennellii CATCATTAAATAGAAGGGGTTAGTTAGAATTTAGTAATACATTCAAAAAAAAAACTCACC
            *********************************************  **      **  *

M82         AATTCAATGTATCTTCATATATTAATGTGGTCATATCAACCTTTGAACATATTAAACAATA
Heinz1706   AATTCAATGTATCTTCATATATTAATGTGGTCATATCAACCTTTGAACATATTAAACAATA
S.pennellii CATTCAATGTATCTTCATATTAATGTGGTCATATTATCTTTGAACATATTAAACAATA
            ***************** *  ****************   * ******************

M82         TAATAGAGAAATAAAATTTGTAAATATCGATATTCTACTTCAACTAGACAATTACATTGT
Heinz1706   TAATAGAGAAATAAAATTTGTAAATATCGATATTCTACTTCAACTAGACAATTACATTGT
S.pennellii TAATAGAAAAATAAAATTTGTAAATGTCGATATTCTACTTCAAGTAGACAATTACATTGT
            ******* ***************** ***************** ***************

M82         TTGTATTCACAATTTTGATAAAGTAATGAGAAGTAAATTAATAGAATACAATAGGAATTT
Heinz1706   TTGTATTCACAATTTTGATAAAGTAATGAGAAGTAAATTAATAGAATACAATAGGAATTT
S.pennellii TTGTATTCACAATTTTGATAAAGTAATGAGAAGTAAATTAATAGAATACAATAGGAATTT
            ************************************************************

M82         GTATATCCATCGTTAAAAGTCAAGAGATAAAACAAACTTT-ATGTATTTAATTATCTAAG
Heinz1706   GTATATCCATCGTTAAAAGTCAAGAGATAAAACAAACTTT-ATGTATTTAATTATCTAAG
S.pennellii GTATATCCATCGTTAAAAGTCAAGAGATAAAACAAACTTTTATGTATTTAATTATCTTAG
            **************************************** *************** **
```

FIG. 8F

M82 and Heinz 1706: SEQ ID NO: 5
S. pennellii: SEQ ID NO: 6

```
M82           AGTCAATTAACTAATTGTATGTTAATATGATGGTTAGGTGAAGAAAACATGTTATAGTAA
Heinz1706     AGTCAATTAACTAATTGTATGTTAATATGATGGTTAGGTGAAGAAAACATGTTATAGTAA
S.pennellii   AGTCAATTAACTAATTGTATGTTAATATGATGGTTAGGTGAAGAAAACATGTTATAGTAA
              ************************************************************

M82           TATTGTATGAGGAAAATATGAAGAAAATGACTGAATTCTCTTGTTCAGTAAAGCAGACAG
Heinz1706     TATTGTATGAGGAAAATATGAAGAAAATGACTGAATTCTCTTGTTCAGTAAAGCAGACAG
S.pennellii   TATTATATGAGGAAAATATGAAGAAAATGACTGAATTCTCTTGTTCAGTAAAGCAGACAG
              **** *******************************************************

M82           CCAATCACACATGTTAAGTGGCCTACTCTCCACTTTTTT-AGTGGACCTTATGCTTCACTAA
Heinz1706     CCAATCACACATGTTAAGTGGCCTACTCTCCACTTTTTT-AGTGGACCTTATGCTTCACTAA
S.pennellii   CAAATCACACATGTTAAGTGGCCTACTCTCCATTTTTTTTTAGTGGACCTTGTCTTCACTAA
              * ****************************** ******* ********** ********

M82           CTTTT--TTTTTTTTTTACCAAAAGCAATAATTTTAATCCAAACAGTAAACAAAAAAAAA
Heinz1706     CTTTT--TTTTTTTTTTACCAAAAGCAATAATTTTAATCCAAACAGTAAACAAAAAAAAA
S.pennellii   CTTATATTTTTTTTTTTACCAAAAGCAATAATTTTAATCCAAACAGTAAACACAAAAGAAA
              ***  * ********************************************* **** ***

M82           A-CATACCACCAACTCACATATACAGGAAGTAACTGTGCACAATGGAAGAAGGAAAATGGA
Heinz1706     --CATACCACCAACTCACATATACAGGAAGTAACTGTGCACAATGGAAGAAGGAAAATGGA
S.pennellii   CACATACCACCAACTCACATATACAGGAAGTAACTGTGCACAATGGAAGAAGGAAAAGGA
                ***************************************************** ***

M82           GCGATCCACTGCTGCTTCGAGATGTTATTATTACAATTTTCAGATTGAACTGAATATACT
Heinz1706     GCGATCCACTGCTGCTTCGAGATGTTATTATTACAATTTTCAGATTGAACTGAATATACT
S.pennellii   GCGATCCACTGCTACTTCGCGATGTTATTATTAGAATTTTCAGATTGAACTGAATATACT
              ************* ***** ************* **************************
```

FIG. 8G

M82 and Heinz 1706: SEQ ID NO: 5
S. pennellii: SEQ ID NO: 6

```
M82          GCTTTCAAGTCATGAACGTGAGAGATAAAATAATAATATTAGGCAGATAGAGGGAGTGATAT
Heinz1706    GCTTTCAAGTCATGAACGTGAGAGATAAAATAATAATATTAGGCAGATAGAGGGAGTGATAT
S.pennellii  GCTTTCAAGTCATGAACGTGAGAGATAAAATAATAATATTAGGCAGAGAGAGAGTGATAT
             ******************************************       ***********

M82          ATACTTCATTAGTCTCCCATTTATATAATTATTTTCTTTTTCATCAGTAAACAAAAAAAA
Heinz1706    ATACTTCATTAGTCTCCCATTTATATAATTATTTTCTTTTTCATCAGTAAACAAAAAAAA
S.pennellii  ATACTTCATTGATCTC--------------------------TTTAATCAGTAA-CAAAAAAGA
             **********  ****                          *** ********* *********  *

M82          AGAAAATATTTTTATATTTAATAACAAATTAATTTTTAAATAAATCAGAACAGATAGAAT
Heinz1706    AGAAAATATTTTTATATTTAATAACAAATTAATTTTTAAATAAATCAGAACAGATAGAAT
S.pennellii  ATAAAACATTTCTATATTTAATAACAAATTAATTTTTAAATATATCAGAACAGATAGAAT
             * **** **** ****************************** ****************

M82          GCCACTATGCAATTGAAAAGAACAAAAAACGAATGAAAAGCAGACGCATTACTAATATT
Heinz1706    GCCACTATGCAATTGAAAAGAACAAAAAACGAATGAAAAGCAGACGCATTACTAATATT
S.pennellii  GCCACTATGCAATTGAAAAGAACAAAAAACGAATGAAAAGCAGACGCATTACTAATATT
             ************************************************************

M82          CCCACCAAGAAATCAATTATGACCAATCTTTGACAAAACAACAATTCTTGGTTTGATATT
Heinz1706    CCCACCAAGAAATCAATTATGACCAATCTTTGACAAAACAACAATTCTTGGTTTGATATT
S.pennellii  CCCACCAAGAAATCAATTATGACCAATCTTTGACAAAACAACAATTCTTGGTTTGATGTT
             ********************************************************  **

M82          TATAAAAGGGTAGTCTAACCCCATTATACATCATCTTGAGGCCTAACAAAACACTCCAAG
Heinz1706    TATAAAAGGGTAGTCTAACCCCATTATACATCATCTTGAGGCCTAACAAAACACTCCAAG
S.pennellii  TATAAAAGGGTACTCTAACCCCATTATACATCATCTTGAGGCCTAACAAAACACTCCAAG
             ************ ***********************************************
```

FIG. 8H

M82 and Heinz 1706: SEQ ID NO: 5
S. pennellii: SEQ ID NO: 6

```
M82          CAGCAAAAATAACATTTTCTTCTTGTTCATCTCTAAGTTCTTTTTAGCTATGGGATCGACAGC
Heinz1706    CAGCAAAAATAACATTTTCTTCTTGTTCATCTCTAAGTTCTTTTTAGCTATGGGATCGACAGC
S.pennellii  CAGCAAAAATAACATTTTCTTCTTGTTCATCTCTAAGTTCTTTTTAGCTATGGGATCGACAGC
             ****************************************************************

M82          AAATATCCAGTTAGCAACAACAATCGGAAGAGACGAAGAGAGCGTAATTGCACGTACGCCATGCA
Heinz1706    AAATATCCAGTTAGCAACAACAATCGGAAGAGACGAAGAGAGCGTAATTGCACGTACGCCATGCA
S.pennellii  AAATATCCAGTTACCAACAACAATCGGAAGAGACGAAAACGTAATTGCACGTACGCCATGCA
             *************  **********************       ********************

M82          ACTACTCTCATCGTCAGTGCTTCCCCTTCGTTTTGCACTCAACTATCCAATTGGATGTTTT
Heinz1706    ACTACTCTCATCGTCAGTGCTTCCCCTTCGTTTTGCACTCAACTATCCAATTGGATGTTTT
S.pennellii  ACTACTCTCATCGTCAGTGCTTCCCCTTCGTTTTGCACTCAACTATCCAATTGGATGTTTT
             ****************************************************************

M82          TGACATACTCGCAAAAGATAAAGCCGCCACTAAACTATCTGCTTTAGAAATTGTGTCTCA
Heinz1706    TGACATACTCGCAAAAGATAAAGCCGCCACTAAACTATCTGCTTTAGAAATTGTGTCTCA
S.pennellii  TGAGATACTCGCAAAAGATAAAGCCGCCACTAAACTATCTGCTTTAGAAATTGTGTCTCA
             *** ************************************************************

M82          CATGCCTAACTGTAAGAACCCTGATGCCGCTACCATGCTAGACCGGATGCTTTATGTCCT
Heinz1706    CATGCCTAACTGTAAGAACCCTGATGCCGCTACCATGCTAGACCGGATGCTTTATGTCCT
S.pennellii  CATGCCTAACTGTAAGAACCCTGATGCCGCTACCATGCTAGACCGGATGCTTTATGTCCT
             ****************************************************************

M82          AGCTAGTTATTCTTTACTCGATTGCTCGGTTGTTGTTGAAGAGGAAATGGGGTGACCGAAAG
Heinz1706    AGCTAGTTATTCTTTACTCGATTGCTCGGTTGTTGTTGAAGAGGAAATGGGGTGACCGAAAG
S.pennellii  AGCTAGTTATTCTTTACTCGATTGTTACTGTGTTGTTGAAGAGGAAATGGGGTGACCGAAAG
             ************************  *  *********************************
```

FIG. 8I

M82 and Heinz 1706: SEQ ID NO: 5

S. pennellii: SEQ ID NO: 6

```
M82          GCGCCTATGGTCTGTCACGAGTGGGGAAATTTTTGTACGTGATGAAGATGGTGCATCCAT
Heinz1706    GCGCCTATGGTCTGTCACGAGTGGGGAAATTTTTGTACGTGATGAAGATGGTGCATCCAT
S.pennellii  GCGCCTATGGTCTGTCACGAGTGGGGAAATTTTTGTACGTGATGAAGATGGTGCATCCAT
             ************************************************************

M82          GGGACCATTGTTGGCTTTGCTTCAAGATAAAGTATTCATTAACAGCTGGTCAGTTTTCTC
Heinz1706    GGGACCATTGTTGGCTTTGCTTCAAGATAAAGTATTCATTAACAGCTGGTCAGTTTTCTC
S.pennellii  GGGACCATTGTTGGCTTTGCTTCAAGATAAAGCATTCATTAACAGCTGGTCAGTTTTCTC
             ******************************** ***************************

M82          TTTTTACTGCAGCAATCTTTCTTTTTAACCAAACTTTTATCATGTCAATTGTATGTGGTC
Heinz1706    TTTTTACTGCAGCAATCTTTCTTTTTAACCAAACTTTTATCATGTCAATTGTATGTGGTC
S.pennellii  TTTTTACTGCAGCAATCTTTCTTTTTAACCAAACTTTTATCATGTCAATTGTATGTGGTC
             ************************************************************

M82          ATCCTAGTATAACCTAACAAATTGAGTATATATATTAGAGATTTTCTCACAATATAAGTGAG
Heinz1706    ATCCTAGTATAACCTAACAAATTGAGTATATATATTAGAGATTTTCTCACAATATAAGTGAG
S.pennellii  ATCCTAGTATAACCTAACAAATTGAGTATATATATTAGAGATTTTCTCACAATATGTGTGAG
             ******************************************************  *****

M82          TCAGAGTCAGGTGGATATATCATGCAAAGTTGAAGACCCCTTTTTTGATCCCTTCATTATA
Heinz1706    TCAGAGTCAGGTGGATATATCATGCAAAGTTGAAGACCCCTTTTTTGATCCCTTCATTATA
S.pennellii  TCAGAGTCAGGTGGATATATCATGCAAAGTTGAAGACCCCTTTTTTGATCCCTTCATTATA
             ************************************************************

M82          TTCTTAATATACAAAACATGTATCTTTGCTGGCTATTATATTAGGGCGGCC-AAATAGAT
Heinz1706    TTCTTAATATACAAAACATGTATCTTTGCTGGCTATTATATTAGGGCGGCC-AAATAGAT
S.pennellii  TTCTTAATATACAAAACATGTATCTTTGCTGGCTATTATATTAGGGCGGCCCAAATAGAT
             *************************************************** ********
```

FIG. 8J

M82 and Heinz 1706: SEQ ID NO: 5

S. pennellii: SEQ ID NO: 6

```
M82          AATTATTCCTATATATTACTTCATGAAGGAATCTCAGAATATTAATGCTTTCCTGTCGAA
Heinz1706    AATTATTCCTATATATTACTTCATGAAGGAATCTCAGAATATTAATGCTTTCCTGTCGAA
S.pennellii  AATTATTCCTATATATTACTTCATGAAGGAATCTCAGAATATTAATGCTTTCCTGTCGAA
             ************************************************************

M82          CCATCTGGTATCCAAAACTCACTAGGCCGACCAATTAAAATCCATGATGCATAGGACCTA
Heinz1706    CCATCTGGTATCCAAAACTCACTAGGCCGACCAATTAAAATCCATGATGCATAGGACCTA
S.pennellii  CCATCCGGTATCCAAAACTCACTAGGCCGACCAATTCAAATCCATGATGCATAGGACCTA
             ***** ****************************** ***********************

M82          TGACAGAGTGAATGAGTCTATTCCTAGCTCGAATCAAAGATTTCTGATCAAGTGTAAAG
Heinz1706    TGACAGAGTGAATGAGTCTATTCCTAGCTCGAATCAAAGATTTCTGATCAAGTGTAAAG
S.pennellii  TTACAGAGTGAATGAGTCTATTCCTAGCTCGAATCAAAGATTTCTGATCAAGTGTGAAG
             * **************************************************** ***

M82          TGATGTGATCATGAGAGACTAATGGAATTTGTAAGTTAATTACAGTTATCATGTTAACAAAT
Heinz1706    TGATGTGATCATGAGAGACTAATGGAATTTGTAAGTTAATTACAGTTATCATGTTAACAAAT
S.pennellii  TGATGTGATCATGAGAGACTAATGGAATTTGTAAGTTAATTACAATTATCATGTTAACAAAT
             ******************************************** *****************

M82          ACATCAACTGGTTCAAGTTAGCATATATAAATTGCTAACAGAATG------------T
Heinz1706    ACATCAACTGGTTCAAGTTAGCATATATAAATTGCTAACAGAATG------------T
S.pennellii  ACATCAACTGGTTCAAGTTAGCATATATAAATTGCTAAGAGAATACTTTTGCATGAGCCTAT
             ************************************** *****           *

M82          GTCCACTCAACTGCCAAAGATCAAGGGTACACTATAATTTCAAGAAATTGTTGGATAGTT
Heinz1706    GTCCACTCAACTGCCAAAGATCAAGGGTACACTATAATTTCAAGAAATTGTTGGATAGTT
S.pennellii  GTCCACTCAACTGCCAAAGATCAAGGGTACACTGTAATTTCGAGAAATTATTGGATAGTT
             ********************************* ******* ****** **********
```

FIG. 8K

M82 and Heinz 1706: SEQ ID NO: 5

S. pennellii: SEQ ID NO: 6

```
M82          AGAGTACGTATGTTATCAGACTCATACTCGTGAAATTACACTGAATATATTGTC-----T
Heinz1706    AGAGTACGTATGTTATCAGACTCATACTCGTGAAATTACACTGAATATATTGTC-----T
S.pennellii  AGGGTACGTATGTTATCAGACTCATACTCGTGAAATTACACTGAATATATTGTTATTAAT
             ** ***************************************************    *

M82          GCTGGATACTTGGGAATTAATTGCTTCCAGATGAGACTGAGGCGTAATTATAGTAGTTGT
Heinz1706    GCTGGATACTTGGGAATTAATTGCTTCCAGATGAGACTGAGGCGTAATTATAGTAGTTGT
S.pennellii  GCTGGATACTTGGGAATTAATTGCTTCCAGATGAGACTGAGGCGTAATTATAGTAGTTGT
             ************************************************************

M82          ATTTCTGACTCTCTCTCTATCTAATTTAAATTACAGGTTTGAACTAAAAGATGCAGTACTTG
Heinz1706    ATTTCTGACTCTCTCTCTATCTAATTTAAATTACAGGTTTGAACTAAAAGATGCAGTACTTG
S.pennellii  ATTTCTGACTCTCTCTCTATCTAATTTAAATTACAGGTTTGAACTAAAAGATGCAGTACTTG
             ************************************************************

M82          AAGGTGGAGTTCCATTTGACAGGGTGCATGGTGTACATGCATTTGAATATCCAAAATTGG
Heinz1706    AAGGTGGAGTTCCATTTGACAGGGTGCATGGTGTACATGCATTTGAATATCCAAAATTGG
S.pennellii  AAGGTGGAGTTCCATTTGACAGGGTGCATGGTGTACATGCATTTGAATATCCAAAATTGG
             ************************************************************

M82          ACCCAAAGTTCAATGATGTTTTCAACCAGGCAATGATAAACCACACAACTGTTGTCATGA
Heinz1706    ACCCAAAGTTCAATGATGTTTTCAACCAGGCAATGATAAACCACACAACTGTTGTCATGA
S.pennellii  ACCCAAAGTTCAATGATGTTTTCAACCAGGCAATGATCAACCACACAACTGTTGTCATGA
             ************************************* **********************

M82          AAAGAATACTTGAAAATTACAAAGGTTTTGAGAATCTCAAAACTTTGGTTGATGTTGGAG
Heinz1706    AAAGAATACTTGAAAATTACAAAGGTTTTGAGAATCTCAAAACTTTGGTTGATGTTGGAG
S.pennellii  AAAGAATACTTGAAAATTACAAAGGTTTTGAGAATCTCAAAACTTTGGTTGATGTTGGAG
             ************************************************************
```

FIG. 8L

M82 and Heinz 1706: SEQ ID NO: 5
S. pennellii: SEQ ID NO: 6

```
M82          GTGGTCTTGGTGTGTTAATCTCAAGATGATTACATCTAAATACCCCACAATTAAGGGCACTA
Heinz1706    GTGGTCTTGGTGTGTTAATCTCAAGATGATTACATCTAAATACCCCACAATTAAGGGCACTA
S.pennellii  GTGGTCTTGGAGTTCTCAAGATGATTACATCTAAATACCCCACAATTAAGGGCACTA
             **********                    ********************************

M82          ATTTTGATTTGCCTCTCATGTTGTTCAACATGCACCTTCCTATCCTGGTACCTTAATTCTTG
Heinz1706    ATTTTGATTTGCCTCTCATGTTGTTCAACATGCACCTTCCTATCCTGGTACCTTAATTCTTG
S.pennellii  ATTTTGATTTGCCTCTCATGTTGTTCAACATGCAACTTCCTATCCTGGTACCTTAATTCTTG
             ********************************* **************************

M82          TTTTATTGTTCACTTTGATACTTTGTTTGTTCAATGTTAGAGAGATTTATACTTTGTTTCAATGT
Heinz1706    TTTTATTGTTCACTTTGATACTTTGTTTGTTCAATGTTAGAGAGATTTATACTTTGTTTCAATGT
S.pennellii  TTTTATTGTTCAATTTGATACTTTGTTTCA--------------------------ATGT
             ************ ***************                            ****

M82          TAGAGATTTAAATTACAATTCATTGGATTGTTTTGTTTGTTGCAAACAAGTTATACAGAGATT
Heinz1706    TAGAGATTTAAATTACAATTCATTGGATTGTTTTGTTTGTTGCAAACAAGTTATACAGAGATT
S.pennellii  TAGAGATTTAAATTACAATTCATTGGATTGTTTTGTTTGTTGCAAACAAGTTATGCAGAGATT
             ****************************************************** *******

M82          ATAATACGAGGTTTAAAATAATAATAACGAGATTCTTTAATCGATAGATTTCTAAAATGGTAG
Heinz1706    ATAATACGAGGTTTAAAATAATAATAACGAGATTCTTTAATCGATAGATTTCTAAAATGGTAG
S.pennellii  ATAATACGAGGTTTAAAATAATAATAACGAGATTCTTTAATCGATAGATTTCTAAAATGGTAG
             ***************************************************************

M82          CTCTCAATTTCCTAACATGAACTGAATTTGTCTTAATAAATATTGCAGGGGTGGATCATG
Heinz1706    CTCTCAATTTCCTAACATGAACTGAATTTGTCTTAATAAATATTGCAGGGGTGGATCATG
S.pennellii  ----------------------------------------CAGGGGTGGATCATG
                                                     ***************
```

FIG. 8M

M82 and Heinz 1706: SEQ ID NO: 5

S. pennellii: SEQ ID NO: 6

```
M82         TTGGGGGAGATATGTTTGAAAGTGTTCCACAAGGAGAGATGCTATTTTTATGAAGGTAATGT
Heinz1706   TTGGGGGAGATATGTTTGAAAGTGTTCCACAAGGAGAGATGCTATTTTTATGAAGGTAATGT
S.pennellii TTGGGGGAGATATGTTTGAAAGTGTTCCACAAGGAGAGATGCTATTTTTATGAAGGTAATGT
            ************************************************************

M82         CCAAATCTTTAGCAGAGGCTGTATGTATGTACTGTGCATATATTTGGCTTACATGTCGAA
Heinz1706   CCAAATCTTTAGCAGAGGCTGTATGTATGTACTGTGCATATATTTGGCTTACATGTCGAA
S.pennellii CCAAATCTTTAGCAGAGGCAATATGTATGTACTGTGCATATATTTGGCTTACATGTCGAA
            *******************  ***************************************

M82         AGTCTTCTTTAATTTCTTAGATTTTGTGTTCAGTCAAACAAACTTTATTTTGTTCCTCAC
Heinz1706   AGTCTTCTTTAATTTCTTAGATTTTGTGTTCAGTCAAACAAACTTTATTTTGTTCCTCAC
S.pennellii AGTCTTCTTTAATTT-TTAGATTTTGTGTTCAGTCAAACAAACTTTATTTTGTTCCTCAC
            *************** ********************************************

M82         ATAACCGATGCGAGTTATGTAACGCTTCTTTTTGTTTGTTTCACAAATTAGCGGACCTAAATTC
Heinz1706   ATAACCGATGCGAGTTATGTAACGCTTCTTTTTGTTTGTTTCACAAATTAGCGGACCTAAATTC
S.pennellii ATAACCGATGCGAGTTATGTAACGCTTCTTTTTGTTTGTTTCACAAATTAGCGGACCTAAATTC
            ****************************************************************

M82         AATACTTTTGGGTTCACAAACTTTGGGTTGACCGATTTATGAAATAAAAAGAAGTCGCT
Heinz1706   AATACTTTTGGGTTCACAAACTTTGGGTTGACCGATTTATGAAATAAAAAGAAGTCGCT
S.pennellii AATACTTCTCGGGTTCACAAACTTTGGGTTGACCAATTTATGAAATAAAAAGAAGTCGCG
            *******  *************************.************************

M82         CACAACTTGTGTCAGCTGGAACTTAACTACTTGCATAGTCTTGCATTCCTGTTCTTCACC
Heinz1706   CACAACTTGTGTCAGCTGGAACTTAACTACTTGCATAGTCTTGCATTCCTGTTCTTCACC
S.pennellii CACAACTTGTGTCAGCTGGAACTTAACTACTTGCATAGTCTTGCATTCCTGTTCTTCACC
            ************************************************************
```

FIG. 8N

M82 and Heinz 1706: SEQ ID NO: 5
S. pennellii: SEQ ID NO: 6

```
M82          AATAGTATCTATAACCTATGATTAATAATAAGGGCATTCTGTGTTTATTGATGAAAAGTGGAT
Heinz1706    AATAGTATCTATAACCTATGATTAATAATAAGGGCATTCTGTGTTTATTGATGAAAAGTGGAT
S.pennellii  AATAGTATCTATAACCTATGATTAATAATAAGGACATTCTGTGTTTATTGATGAAAAGTGGAT
             ********************************* ******************************

M82          CCTTCATGACTGGAGTGATGGTCACTGCCTCAAATTGCTGAAGAACTGTCATAAGGCTCT
Heinz1706    CCTTCATGACTGGAGTGATGGTCACTGCCTCAAATTGCTGAAGAACTGTCATAAGGCTCT
S.pennellii  CCTTCATGACTGGAGTGATGGTCACTGCCTCAAATTGCTGAAGAACTGCCATAAGGCTCT
             ************************************************ ***********

M82          ACCGGACAACGGAAAAGGTGATTGTTGTGTGGAGGCCAATCTACCAGTGAAACCTGATACTGA
Heinz1706    ACCGGACAACGGAAAAGGTGATTGTTGTGTGGAGGCCAATCTACCAGTGAAACCTGATACTGA
S.pennellii  ACCGGACAACGGAAAAGGTGATTGTTGTGTGGAGGCCAATCTACCAGTGAAACCTGATACTGA
             ****************************************************************

M82          TACCACAGTGGTTGGAGTTTCACAATGTGATTTGATCATGATGGCTCAGAATCCCGGAGG
Heinz1706    TACCACAGTGGTTGGAGTTTCACAATGTGATTTGATCATGATGGCTCAGAATCCCGGAGG
S.pennellii  TACCACAGTGGTTGGAGTTTCACAATGTGATTTGATCATGATGGCTCAGAATCCCGGAGG
             **************************************************  *****

M82          TAAAGAGCGTTCTGAACAGGAGTTTCGGGCATTGGCAAGTGAAGCTGGATTCAAAGGTGT
Heinz1706    TAAAGAGCGTTCTGAACAGGAGTTTCGGGCATTGGCAAGTGAAGCTGGATTCAAAGGTGT
S.pennellii  CAAAGAGCGTTCTGAACAGGAGTTTCGGGCATTGGCAAGTGAAGCTGGATTCAAAGGTGT
             ************************************************************

M82          TAACCTAATATGTTGTCTGTCTGTAATTTTTGGGTCATGGAATTTTACAAGTAGATTTCCAC
Heinz1706    TAACCTAATATGTTGTCTGTCTGTAATTTTTGGGTCATGGAATTTTACAAGTAGATTTCCAC
S.pennellii  TAACCTAATATGTTGTCTGTCTGTAATTTTTGGGTCATGGAATTTTACAAGTAGATTTCCAC
             *************************************************************
```

FIG. 8O

M82 and Heinz 1706: SEQ ID NO: 5
S. pennellii: SEQ ID NO: 6

```
M82         AACCTACTTCGCTCTTATGATTATGTATTTTCGTGGCACTCTGGGACTGGAATTTATAAA
Heinz1706   AACCTACTTCGCTCTTATGATTATGTATTTTCGTGGCACTCTGGGACTGGAATTTATAAA
S.pennellii AACCTACTTCGCTCTTATGATTATGTACTTTCGTGGCACTCTGGGACTGGAATTTATAAA
            ************************** *********************************

M82         CTAGCCCAGCTTGAATGTTTGACGTTGATTCCTAATAATATATTTATATTACTACTTGTTTG
Heinz1706   CTAGCCCAGCTTGAATGTTTGACGTTGATTCCTAATAATATATTTATATTACTACTTGTTTG
S.pennellii TTAGCCCAGCTTGAATGTTTGACGTTGATTCCTAATAATATATTTATATTACTACTTGTTTG
             ***********************************************************

M82         TTTCTCTAGTTTTGAGAGGATGTCATTAACTTCATTGTAACTTCTGTCTCTTAATAATATTTAT
Heinz1706   TTTCTCTAGTTTTGAGAGGATGTCATTAACTTCATTGTAACTTCTGTCTCTTAATAATATTTAT
S.pennellii TTTCTCTAGTTTTGAGAGGATGTCAT------TGTAACTTCTGTCTCTTAATAATATTTAT
            *************************      *****************************

M82         ATATTCCTCTGTTCCATTTGATATGATGCCTTCCTTTTTTAGTTTTTCAGAAAAAAGAATGA
Heinz1706   ATATTCCTCTGTTCCATTTGATATGATGCCTTCCTTTTTTAGTTTTTCAGAAAAAAGAATGA
S.pennellii ATATTCCTCTGTTCCATTTGATATGATGCCTTCCTTTTTTAGTTTTTCAGCAAAA-GAATGA
            **************************************************  **** ******

M82         ACCCAAACATACGTAACCCGTCCAATCCGCCCCAGAATTTTAAGGGTTGGGCTCAAGATAA
Heinz1706   ACCCAAACATACGTAACCCGTCCAATCCGCCCCAGAATTTTAAGGGTTGGGCTCAAGATAA
S.pennellii ACCCAAACATACGTAACCCGTCCAATCCGCCCCAGAATTTTAAGGGTTGGGCTCAAAATAA
            ********************************************************  ****

M82         TTTGAAATGGGTTCAATCTCAACCATTCAAGCAAAGAGAATTCTCAATTGAGCCCAATT
Heinz1706   TTTGAAATGGGTTCAATCTCAACCATTCAAGCAAAGAGAATTCTCAATTGAGCCCAATT
S.pennellii TTTGAATTGGGTTCAATCTCAACCATTCAAGCAA-GAAAATTCTCAATTGAGCCCAATT
            ******  **************************  ** ********************
```

FIG. 8P

M82 and Heinz 1706: SEQ ID NO: 5

S. pennellii: SEQ ID NO: 6

```
M82         CAATCTCCAATTTCAACCCGTTTTAAAAAAATTTATTAAGATATGTTCCTATATTGAAAG
Heinz1706   CAATCTCCAATTTCAACCCGTTTTAAAAAAATTTATTAAGATATGTTCCTATATTGAAAG
S.pennellii CAATCTCCAATTTCAACCCGTTTTAAATTTTTTATTAAGATATGTTCCTATATTGAAAG
            *************************** * *****************************

M82         TATGAATTATTATCTATTTAACATCTTTTAGAATTTATCTATCAATTTGTTACTTTTTTA
Heinz1706   TATGAATTATTATCTATTTAACATCTTTTAGAATTTATCTATCAATTTGTTACTTTTTTA
S.pennellii TATGAGTTATTATTATTTAACATCTCTCGGGATTTATCTATCAATTTGTTATTTTTTTA
            ***** ******* * ********* *  * ******************* ********

M82         ACAAAAAAATTCTTGAGCCGAAATTCAAATTGTGATTATAAAAGTTATATATCAATATGTT
Heinz1706   ACAAAAAAATTCTTGAGCCGAAATTCAAATTGTGATTATAAAAGTTATATATCAATATGTT
S.pennellii ACAAAAAAATTCTTGAGTCGAAATTCAAATTGTGATTATAAAAGTTATATATCAATATGTT
            ***************** ******************************************

M82         AAATTATTGAGATTAATCGGATCAAATTGGGTAGGTCAA-GACCAACCCCGTTTTTTAGC
Heinz1706   AAATTATTGAGATTAATCGGATCAAATTGGGTAGGTCAA-GACCAACCCCGTTTTTTAGC
S.pennellii AAATTATTGTGATTAATCGGGTCAAATTGGGCAGGTCAAAGACCAAACCAAACCCGTTTTTTAGC
            ********* ********** ********** ******* *******  *  ** *************

M82         CCATTTGA------------ACCCAAAGTAAACTTGGGCGGGTCGAGACCAACCCA
Heinz1706   CCATTTGA------------ACCCAAAGTAAACTTGGGCGGGTCGAGACCAACCCA
S.pennellii CCATTTGAGCCCCAACCCATTTGAACCCAAAGTAAACTTGGGCGGGTCGAGACCAACCCA
            ********            ***************************************

M82         ATTTCTATTCAACCCATTGTAATATTTAAATTTCAACC--ACCCGCCCATTTGACACCC
Heinz1706   ATTTCTATTCAACCCATTGTAATATTTAAATTTCAACC--ACCCGCCCATTTGACACCC
S.pennellii ATTTCTATTCAACCCATTGTAATATTTTAAATTTCAACCCAACCCGCCCATTTGACACCC
            *************************** ********** *******************
```

FIG. 8Q

M82 and Heinz 1706: SEQ ID NO: 5

S. pennellii: SEQ ID NO: 6

```
M82          CTAATTATTATTTTTATTTTCATATTTCCTTTTTCAAACTGCTTTGGGGTGCTTTAGGAA
Heinz1706    CTAATTATTATTTTTATTTTCATATTTCCTTTTTCAAACTGCTTTGGGGTGCTTTAGGAA
S.pennellii  CTAATTATTATTTTTATTTTCATATTTCCTTTTTCAAACTGCTTTGGGATGCTTTAGGAA
             *********************************************  ************

M82          ACCACACTTTGTCTCTACGAGGTAGGAATAAGGTCTATGTACACTCTACCCTACCCAGAC
Heinz1706    ACCACACTTTGTCTCTACGAGGTAGGAATAAGGTCTATGTACACTCTACCCTACCCAGAC
S.pennellii  ACCACACTTTGTCTCTACGAAGTAGGAATAAGGTTTATGTACAATCTACCCTACCCAGAC
             ********************  ************  ********  **************

M82          TATACTTGTGTGAGATTACACTGGATATGCATCCAGTTGTTGTTGTTCTAGACTCTA
Heinz1706    TATACTTGTGTGAGATTACACTGGATATGCATCCAGTTGTTGTTGTTCTAGACTCTA
S.pennellii  TACACTTGTGAAATTAC------------------GTTATTGTTGGGTTCTAGACTCTA
             ** ********  *****                   ***  ****** **********

M82          ATCTTTTCAAGTTACTAGGAGTAACTTGTACAAATTCAAATCAACTTTTGTAACAAACAT
Heinz1706    ATCTTTTCAAGTTACTAGGAGTAACTTGTACAAATTCAAATCAACTTTTGTAACAAACAT
S.pennellii  ATCTTTTCAAGTTACTAGGAGTAACTTGTACAAATTCAA-TCAACTTTTGTAACAATCAT
             ***************************************  ***************  ***

M82          GGAGTTTGAGCAGCCAAAGATACTGGCTTTAGCCGAGCCCATACCCTCCCTCCTCCACCC
Heinz1706    GGAGTTTGAGCAGCCAAAGATACTGGCTTTAGCCGAGCCCATACCCTCCCTCCTCCACCC
S.pennellii  GGAATTTGAGCAGCCAAAGATACTGGCTTTGCTTTAGCCGAGCCCATACCCTCCCTCCTCCACCC
             ***  *************************  *  *************************

M82          CTACTAGGATGAGGCATTGCCTCTTCACGATTTGGACTATATAGCTATTGGACTATATAAC
Heinz1706    CTACTAGGATGAGGCATTGCCTCTTCACGATTTGGACTATATAGCTATTGGACTATATAAC
S.pennellii  CTACTAGGATGAGGCATTGCCTCTTCACGATTTGGACTGATGTATAGCTATTGGACTATATAAC
             ************************************************************
```

FIG. 8R

M82 and Heinz 1706: SEQ ID NO: 5

S. pennellii: SEQ ID NO: 6

```
M82          CATAGT------AACATGTTTTATTGCACAAGTTCTTTTAAGCCATTGAATTAGCAAAG
Heinz1706    CATAGT------AACATGTTTTATTGCACAAGTTCTTTTAAGCCATTGAATTAGCAAAG
S.pennellii  CATAGTCCATAGTAACATGTTTTATTGCACAAGTTCTTTTAAGCCATTGAATTAGCAAAG
             ******      ************************************************

M82          ATATGGATTTACTTGAAAGCATTTGATATACATTAACTTCCAACTGCTAATGAGAACATA
Heinz1706    ATATGGATTTACTTGAAAGCATTTGATATACATTAACTTCCAACTGCTAATGAGAACATA
S.pennellii  ATATGGATTTACTTGAAAGCATTTGATATACATTAACTTCCAACTGCTAACGAGAACATA
             **************************************************  ********

M82          TTGAAGGTGAGGAAATGAAAAGACAATATACAGATAAGCACATATATAGACATAGTTCAG
Heinz1706    TTGAAGGTGAGGAAATGAAAAGACAATATACAGATAAGCACATATATAGACATAGTTCAG
S.pennellii  TTGAAGGTGAGGAAATGAAAAGACAATATACAGATAAGCACATATATAGACATAGTTCAG
             ************************************************************

M82          TTTGGGTTTTATTCTGTTAGAATAAAAAGACAAAAAGATCGAAGCAGAGTTTACATTTGAA
Heinz1706    TTTGGGTTTTATTCTGTTAGAATAAAAAGACAAAAAGATCGAAGCAGAGTTTACATTTGAA
S.pennellii  TTGG-TTTTATTCTGTTAGAATAAAAAGACAAAAAGATCGAAGCAGAGTTTACATTTGAA
             **   *******************************************************

M82          GAGCAAAGCTGCAAGATTGCTCAACTGAAATCTATTTTGACCATGTCTCTGCAGCAGCAT
Heinz1706    GAGCAAAGCTGCAAGATTGCTCAACTGAAATCTATTTTGACCATGTCTCTGCAGCAGCAT
S.pennellii  GAGCAAAGCTGCAAGATTGCTCAACTGAAATCTATTTTGACCATGTCTCTGCAGCAGCAT
             ************************************************************

M82          CGGACTATGTTTCCATTTAGCTGCTCCCAAGAATATCCTTGTACAATTCCTTGATTTTTG
Heinz1706    CGGACTATGTTTCCATTTAGCTGCTCCCAAGAATATCCTTGTACAATTCCTTGATTTTTG
S.pennellii  CGGACTATGTTTCCATTTAGCTGCTCCCAAGAATATCCTTGTATAATTCCTTGATTTTTG
             ****************************************** ****************
```

FIG. 8S

M82 and Heinz 1706: SEQ ID NO: 5
S. pennellii: SEQ ID NO: 6

```
M82         CTATCAAAGCTTCTCTCTGTTAGCAGCAAAAGGTAATAAGAAGAGAGAGGTAAGCTAGGATGAA
Heinz1706   CTATCAAAGCTTCTCTCTGTTAGCAGCAAAAGGTAATAAGAAGAGAGAGGTAAGCTAGGATGAA
S.pennellii CTATCAAAGCTTCTCTCTGTTAGCAGCAAAAGGTAATAAGAAGAGAGAGGTAAGCTAGGATGAA
            ****************************************************************

M82         CACACAAAGGTATGAATAATAAACTTAACTTCCACTAGTTCATATACAAAGGAACGGAAA
Heinz1706   CACACAAAGGTATGAATAATAAACTTAACTTCCACTAGTTCATATACAAAGGAACGGAAA
S.pennellii CACACAAAGGTATGAATAATAAACTTAACTTCCACTAGTTCATATACAAAGGAACGGAAA
            ************************************************************

M82         TAACCTGTCAGGTTTGAAGATCAAGTTCTTGTAGGCAAACCACTGCAGAGGAAGGGAAGA
Heinz1706   TAACCTGTCAGGTTTGAAGATCAAGTTCTTGTAGGCAAACCACTGCAGAGGAAGGGAAGA
S.pennellii TAACCTGTCAGGTTTGAAGATCAAGTTCTTGTAGGCAAACCACTGCAGAGGAAGGGAAGA
            ************************************************************

M82         TCCCCCAAAAACGTGTAAATGAAGTCAAGATAACATGGTAATCGATTATATAGTTCAAAG
Heinz1706   TCCCCCAAAAACGTGTAAATGAAGTCAAGATAACATGGTAATCGATTATATAGTTCAAAG
S.pennellii TCCCCCAAAAACGTGTAAATGAAGTCAAGATAACATGGTAATCGATTATATAGTTCAAAG
            ************************************************************

M82         TTTAACCAAACAAGCATTGATGAAGCCTGATGCTAATGCCTATGCAATATGGTTCAAAGA
Heinz1706   TTTAACCAAACAAGCATTGATGAAGCCTGATGCTAATGCCTATGCAATATGGTTCAAAGA
S.pennellii TTTAACCAAACAAGCATTGATGAAGCCTGATGCTAATGCCTATGCAATATGGTTCAAAGA
            ************************************************************

M82         AAGGATTTAACTTAAGTATAACGTTTATTTTTTACCCTATCAGTGTAATTATTGGTTATA
Heinz1706   AAGGATTTAACTTAAGTATAACGTTTATTTTTTACCCTATCAGTGTAATTATTGGTTATA
S.pennellii AAGGATTTAACTTAAGTATAACGTTTATTTTTTACCCTATCAGTGTAATTATTGGTTATA
            ************************************************************
```

FIG. 8T

M82 and Heinz 1706: SEQ ID NO: 5

S. pennellii: SEQ ID NO: 6

```
M82          GCATTCAGGTTACACAACATACAGAGTAGTGGCTAAGAGTGAAAATATTTCAACTTACACCG
Heinz1706    GCATTCAGGTTACACAACATACAGAGTAGTGGCTAAGAGTGAAAATATTTCAACTTACACCG
S.pennellii  GCATTCAGGTTACACAACATACAGAGTAGTGGTTAAGAGTGAAAATATTTCAACTTACACCG
             ******************************** ***************************

M82          GTGTAACCAATTCCTACAAGCTCAAGAACACCAGGAATCAAAGGAAGCCTGTCAATTGCC
Heinz1706    GTGTAACCAATTCCTACAAGCTCAAGAACACCAGGAATCAAAGGAAGCCTGTCAATTGCC
S.pennellii  GTGTAACCAATTCCTACAAGCTCAAGAACACCAGGAATCAAAGGAAGCCTGTCAATTGCC
             ************************************************************

M82          TGCCACAATTAAGCAAGTCCCCTTTGTCAAAGTTTGTTATAGTTTGCAACACCTGAACTAA
Heinz1706    TGCCACAATTAAGCAAGTCCCCTTTGTCAAAGTTTTGTTATAGTTTGCAACACCTGAACTAA
S.pennellii  TGCCACAATTAAGCAAGTCCCCTTTGTCAA-GTTTGTTATAGTTTGCAACACCTGAACAAA
             ****************************** **** *********************  *

M82          AATGGAACTAAAAAAA-GTCTTAAGGTAGCAATTAGTAGTAGCAGTA
Heinz1706    AATGGAACTAAAAAA-GTCTTAAGGTAGCAATTAGTAGTAGCAGTA
S.pennellii  AATGGAACTAAAAAAAAGTCTTAAGGTAGCAATTAGTAGTAGCAGTA
             *************** ******************************
```

TOMATO CATECHOL-*O*-METHYLTRANSFERASE SEQUENCES AND METHODS OF USE

CROSS-REFERENCE TO RELATED APPLICATIONS

This application claims priority to U.S. provisional application entitled, "Tomato Catechol-O-Methyltransferase," having Ser. No. 61/536,690, filed on Sep. 20, 2011, which is entirely incorporated herein by reference.

STATEMENT REGARDING FEDERALLY SPONSORED RESEARCH OR DEVELOPMENT

This invention(s) was made with government support under Grant No.: IOS-0923312 awarded by the National Science Foundation. The government has certain rights in the invention(s).

BACKGROUND

The tomato is one of the most widely grown and valuable fruit crops world-wide. Despite its popularity and important contribution to human nutrition, the commercially produced fruit is widely viewed as having poor taste and its flavor is a major source of consumer dissatisfaction. Flavor is a complex trait that appears to be driven by the combination of flavor compounds, including certain volatile compounds.

Tomato breeding programs have focused mainly on resistance to biotic and abiotic stress, improved yield, storage quality, and color (Bai and Lindhout 2007). Improving tomato flavor through breeding has proven to be a much more daunting task; flavor is a complex trait that is comprised of a mixture of sugars, acids, and about 30 different volatiles (Baldwin et al 2008; Tieman et al 2006; Klee, 2010). Each volatile has its own biosynthetic pathway, and precursors include amino acids, fatty acids, and carotenoids (Goff and Klee 2006).

Guaiacol (2-methoxyphenol), a volatile compound described as having a smoky or medicinal aroma (Alvarez-Rodriguez et al. 2003), is found in many processed food products such as wine, roasted coffee, tea, cocoa, and food additives like liquid smoke (Bonvehi and Coll 1998; Dorfner et al 2003; Guillen et al. 1995; Hayasaka et al 2010; Kumazawa and Masuda 2002). Guaiacol is not commonly found in fresh fruits and vegetables, but is an important contributor to tomato flavor. Since guaiacol has been described as an undesirable compound in many fruits, based on its medicinal-like aroma (Zierler et al., 2004; Zanor et al., 2009), identifying genes responsible for its synthesis could prove useful in breeding programs focusing on altering tomato flavor.

SUMMARY

Briefly described, embodiments of the present disclosure provide isolated DNA molecules encoding tomato O-methyltransferases (OMT), tomato OMT proteins capable of catalyzing production of guaiacol, OMT antisense molecules capable of inhibiting production of guaiacol, vectors including the OMT DNA or OMT antisense molecules, plant cells and plants including the OMT DNA or OMT antisense molecules, methods of increasing or decreasing the amount of guaiacol produced by a plant, hybrid tomato plants, and genetic markers for tomato OMT genes.

The present disclosure provides isolated DNA molecules encoding a tomato O-methyltransferase (OMT) capable of catalyzing production of guaiacol, where the DNA molecules have at least 90% sequence identity with SEQ ID NO: 2. In embodiments, the isolated DNA molecules encoding a tomato O-methyltransferase (OMT) according to the present disclosure, have the polynucleotide sequence of SEQ ID NO: 2 or SEQ ID NO: 7. The present disclosure also provides isolated peptides having at least 90% sequence identity with SEQ ID NO: 3. In embodiments, such peptides of the present disclosure include peptides having SEQ ID NO: 3 and/or SEQ ID NO: 4.

In embodiments, the present disclosure provides, tomato plants grown from transgenic tomato plant cells transformed with vectors including a DNA molecule encoding a tomato O-methyltransferase (OMT) that catalyzes production of guaiacol, where the DNA molecule has at least 90% sequence identity with SEQ ID NO: 2, and at least one regulatory sequence operatively linked to the DNA molecule such that the OMT is expressed in the transgenic plant cells. In embodiments, such plants of the present disclosure produce fruit that includes more guaiacol than a fruit from a wild type plant of the same variety as the transgenic plant.

Embodiments of the present disclosure also provide isolated antisense polynucleotides, where the antisense polynucleotide is capable of inhibiting expression of an endogenous tomato O-methyltransferase (OMT) gene having at least 90% sequence identity with SEQ ID NO: 2. The present disclosure also provides tomato plants grown from transgenic tomato plant cells transformed with vectors including the antisense polynucleotides of the present disclosure, which are capable of inhibiting expression of an endogenous OMT gene having at least 90% sequence identity with SEQ ID NO: 2, and at least one regulatory sequence operatively linked to the antisense polynucleotide such that the antisense polynucleotide is transcribed in the transgenic plant cells. In embodiments, such plants of the present disclosure produce fruit that includes less guaiacol than a fruit from a wild type plant of the same variety as the transgenic plant.

The present disclosure further provides tomato plants including a plurality of cells including a recombinant polynucleotide having a DNA molecule encoding a tomato O-methyltransferase (OMT) and at least one regulatory sequence operatively linked to the DNA molecule such that the OMT is expressed in the plant cell, where the DNA molecule has at least 90% sequence identity with SEQ ID NO: 2 and the OMT catalyzes production of guaiacol. Such tomato plants of the present disclosure have increased expression of O-methyltransferase (OMT) relative to a wild type plant.

The present disclosure further provides tomato plants including a plurality of cells including a recombinant polynucleotide having an antisense polynucleotide capable of inhibiting expression of an endogenous tomato O-methyltransferase (OMT) gene having at least 90% sequence identity with SEQ ID NO: 2, and at least one regulatory sequence operatively linked to the antisense polynucleotide such that the antisense polynucleotide is transcribed in the plant cell. Such tomato plants of the present disclosure have decreased expression of O-methyltransferase (OMT) relative to a wild type plant.

The present disclosure provides methods for inhibiting the expression of endogenous OMT in a tomato plant, relative to a wild type plant, by integrating into the genome of at least one cell of the plant the antisense vectors of the present disclosure and growing such plant, whereby the antisense polynucleotide in the vector inhibits expression of the tomato OMT gene.

The present disclosure also provides methods for increasing the expression of endogenous O-methyltransferase (OMT) in a tomato plant, relative to a wild type plant, by integrating into the genome of at least one cell of the plant a vector of the present disclosure including an OMT gene that is over-expressed in the cell, and growing said plant, whereby said OMT is over-expressed relative to a wild type plant cell.

Embodiments of the present disclosure also include genetic markers capable of identifying a DNA molecule encoding tomato OMT having at least 90% sequence identity to SEQ ID NO: 2.

In embodiments, the present disclosure also includes methods for altering the production of guaiacol in a tomato plant by identifying a first tomato plant variety that produces fruit with desired levels of guaiacol as compared to a second tomato plant variety; identifying a genetic marker associated with an OMT gene from the first plant variety that is responsible for the altered guaiacol production; and monitoring the marker genotype during breeding with the second tomato plant variety to select for introgression of a genomic fragment responsible for the altered guaiacol production phenotype into the genome the second tomato plant to produce a new line of tomato plants that produce fruit with altered levels of guaiacol as compared to the second tomato plant variety.

The present disclosure also includes hybrid *Solanum lycopersicum* plants having as one of its ancestors a parental *S. lycopersicum* plant, where the hybrid *S. lycopersicum* plant has a genome comprising at least one allele of an OMT gene associated with lower guaiacol production than a plant of the parental *S. lycopersicum* plant, where the allele has been introgressed into the genome of the hybrid *S. lycopersicum* plant from a second *Solanum* species, and where the hybrid *S. lycopersicum* produces fruit having lower levels of guaiacol than the fruit produced by a plant from the parental *S. lycopersicum* variety.

Other compositions, plants, methods, features, and advantages of the present disclosure will be or become apparent to one with skill in the art upon examination of the following drawings and detailed description. It is intended that all such additional compositions, plants, methods, features, and advantages be included within this description, and be within the scope of the present disclosure.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 4A shows increased mRNA levels of SlOMT1 for three lines over-expressing SlOMT1. FIG. 4B shows knockdown of endogenous mRNA levels for three antisense lines. SlOMT1 was expressed under a FMV promoter. Total mRNA was extracted from fruit. Error bars represent standard error.

FIG. 4B shows knockdown of endogenous OMT1 in four antisense lines. SlOMT1 was expressed under a FMV promoter. Total RNA was extracted from fruit. Error bars represent standard error.

FIG. 6A illustrates the spectrum showing the guaiacol peak at 20.65 minutes. An increase in guaiacol emission was observed in both Flora-Dade and SlOMT1$_{OE}$ when fed with catechol. Higher guaiacol production was observed in SlOMT1$_{OE}$ both under control and catechol-fed conditions than Flora-Dade. The table in FIG. 6B summarizes the differences in guaiacol production between Flora-Dade and SlOMT1$_{OE}$.

FIG. 7 shows the sequence alignment between protein sequences for COMT from *S. lycopersicum* (SEQ ID NO: 3) and wild tomato relative *S. pennellii* (SEQ ID NO: 4). The sequences have about 98% identity.

FIGS. 8A-8T show the sequence alignment between nucleotide sequences from *S. lycopersicum* varieties (M82 and Heinz1706, SEQ ID NO: 5) and *S. pennellii* (SEQ ID NO: 6), including the coding regions for COMT (shown in bold, corresponding to SEQ ID NO: 2 for M82 and Heinz1706 and SEQ ID NO: 7 for *S. pennellii*). The coding regions are 100% identical for M82 and Heinz1706, and the coding region for *S. pennellii* has about 99% sequence identity with the other two.

DESCRIPTION

Figure 1:
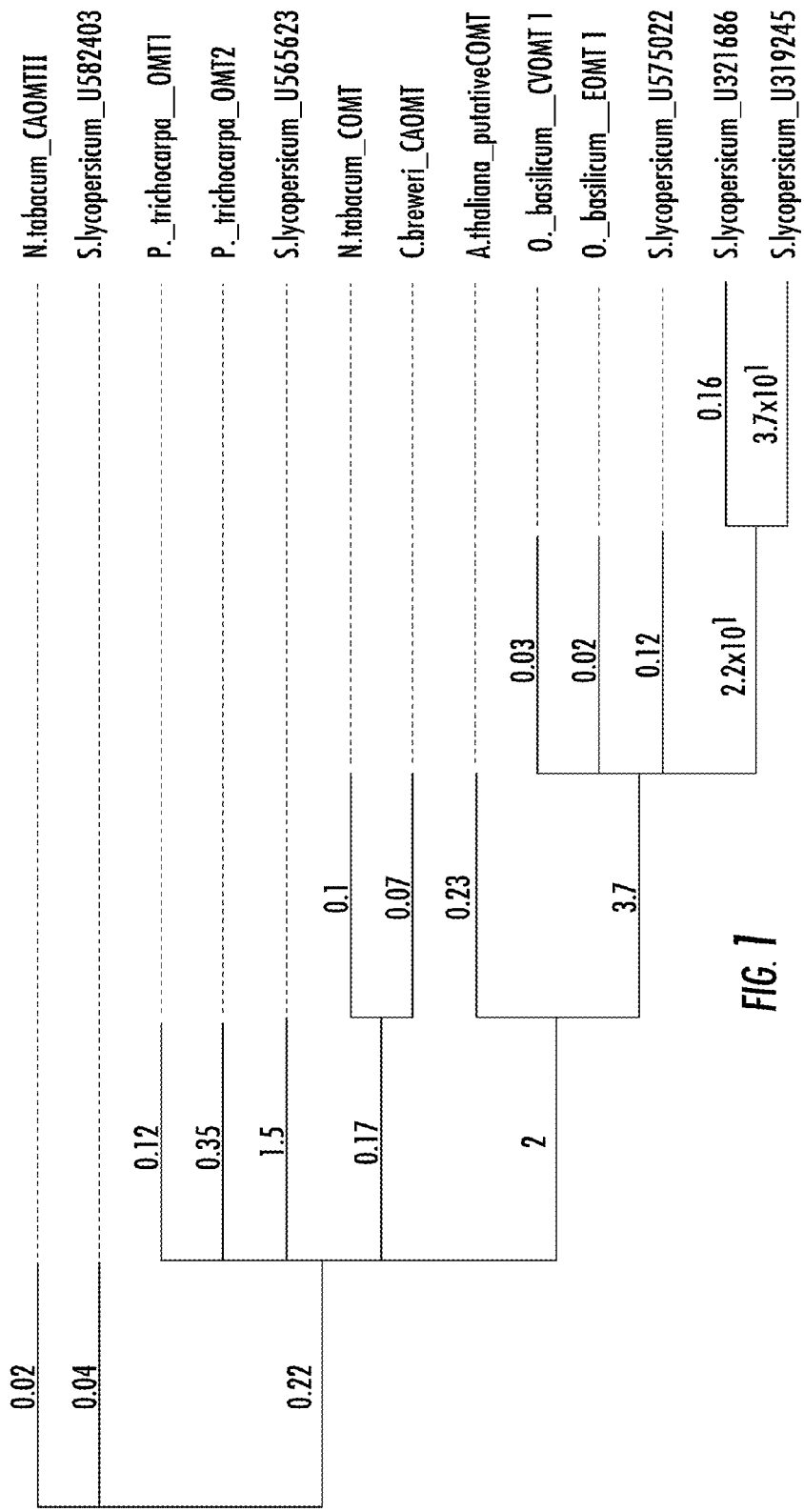
FIG. 1 illustrates a phylogenetic analysis of O-methyltransferase (OMT) related proteins. A non-rooted phylogenetic tree was generated by using the ClustalW. Numbers above branch represents substitutions per site. CAOMT=caffeic acid O-methyltransferase; COMT=catechol O-methyltransferase; CVOMT=Chavicol O-methyltransferase; EOMT=eugenol O-methyltransferase.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of agriculture, botany, organic chemistry, biochemistry, molecular biology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps. Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law, and the term is open-ended, allowing for the presence of more than that which is recited so long as basic or novel characteristics of that which is recited is not changed by the presence of more than that which is recited, but excludes prior art embodiments.

In this specification and in the embodiments that follow, reference will be made to a number of terms that shall be defined to have the following meanings unless a contrary intention is apparent.

DEFINITIONS

In describing the disclosed subject matter, the following terminology will be used in accordance with the definitions set forth below.

As used herein, the term "tomato" or "tomato plant" means any variety, cultivar, or population of *Solanum lycopersicum* (also known as *Lycopersicon esculentum* and/or *Lycopersicon lycopersicum*), including both commercial tomato plants as well as heirloom varieties. In some embodiments, "tomato" may also include wild tomato species, such as, but not limited to, *Solanum lycopersicum* var. *cerasiforme, Solanum pimpineffifolium, Solanum cheesmaniae, Solanum neorickii, Solanum chmielewskii, Solanum habrochaites, Solanum penneffii, Solanum peruvianum, Solanum chilense* and *Solanum lycopersicoides.*

As used herein, the term "plant" includes plant cells, plant protoplasts, plant cell tissue cultures from which tomato plants can be regenerated, plant calli, plant cell clumps, and plant cells that are intact in plants, or parts of plants, such as embryos, pollen, ovules, flowers, leaves, seeds, roots, root tips and the like.

The term "tomato fruit" refers to the fruit produced by a tomato plant, including the flesh, pulp, meat, and seeds of the fruit.

As used herein, the term "variety" or "cultivar" means a group of similar plants within a species that, by structural features, genetic traits, performance, and/or content of volatile compounds, sugars, and/or acids, can be identified from other varieties/cultivars within the same species.

The term "volatile compound" refers to chemicals found in the fruit of the tomato plant that can be sensed by the olfactory systems of a consumer. Some exemplary volatile compounds include, but are not limited to 1-penten-3-one, isovaleronitrile, trans-2-pentenal, trans-2-heptenal, trans-3-hexen-1-ol, 6-methyl-5-hepten-2-ol, nonyl aldehyde, cis-4-decenal, isovaleraldehyde, 3-methyl-1-butanol, methional, 2,5-dimethylhydroxy-3(2H)-furanone, 3-pentanone, 1-pentanol, benzyl cyanide, isovaleric acid, 2-isobutylthiazole, 1-nitro-3-methylbutane, benzaldehyde, 6-methyl-5-hepten-2-one, β-ionone, β-cyclocitral, geranial, phenylacetaldehyde, eugenol, geranylacetone, 2-phenylethanol, neral, salicylaldehyde, isobutyl acetate, butyl acetate, cis-3-hexen-1-ol, 1-nitro-2-phenylethane, 1-penten-3-ol, 2-methylbutyl acetate, heptaldehyde, trans,trans-2,4-decadienal, 2-methylbuteraldehyde, 4-carene, hexyl alcohol, guaiacol, propyl acetate, hexanal, cis-2-penten-1-ol, 2-butylacetate, 1-octen-3-one, cis-3-hexenal, methylsalicylate, trans-2-hexenal, β-damascenone, 2-methyl-1-butanol, 2-methyl-2-butenal, prenyl acetate, hexyl acetate, 3-methyl-1-pentanol, 2-ethylfuran, isopentyl acetate, benzothiazole, cis-3-hexenyl acetate, benzyl alcohol, citric acid, 3-methyl-2-butenal, 2-methylbutanal, and p-anisaldehyde.

The term "flavor-associated compound" refers to chemicals found in the fruit of the tomato plant that can be sensed by the taste and/or olfactory systems of a consumer that include, but are not limited to, volatile compounds, as discussed above, as well as various sugars and acids.

As used herein, the term "hybrid" means any offspring (e.g., seed) produced from a cross between two genetically unlike individuals, including, but not limited to, the cross between two inbred lines (Rieger, R., A Michaelis and M. M. Green, 1968, A Glossary of Genetics and Cytogenetics, Springer-Verlag, N.Y.). An "F1 hybrid" is the first generation offspring of such a cross, while an "F2", "F3" hybrid, and so on, refer to descendent offspring from subsequent crosses (e.g., backcrossing of an F1 hybrid or later hybrid with one of the parent plant varieties, crossing an F1 hybrid with a different plant variety than the original parents, and so on).

As used herein "ancestor" refers to a direct-line genetic predecessor of a plant (e.g., parent, grandparent, great-grandparent, and so-on).

As used herein, the term "inbred" means a substantially homozygous plant, or variety.

As used herein, the terms "introgression" or "introgressed" refers to both a natural and/or artificial process whereby a gene(s) of one species, variety or cultivar are introduced or moved into the genome of another species, variety or cultivar. As used herein, the term "introgressing" means entering or introducing one or more genes from one or more donor or ancestor plants into a recipient or descendent. The process may optionally be complemented by backcrossing to the recurrent parent. In some embodiments, introgression may be accomplished by either traditional breeding techniques or by transgenic methods, or a combination of genetic transformation and traditional breeding.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above. The term "DNA molecule" includes nucleic acids/polynucleotides that are made of DNA.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

A "gene" typically refers to a hereditary unit corresponding to a sequence of DNA that occupies a specific location on a chromosome and that contains the genetic instruction for a characteristic(s) or trait(s) in an organism.

A "locus" refers to the position that a given gene or portion thereof occupies on a chromosome of a given species.

As used herein, the term "allele(s)" means any of one or more alternative forms of a gene, where the alleles relate to at least one trait or characteristic. In a diploid cell or organism, the two alleles of a given gene occupy corresponding loci on a pair of homologous chromosomes.

The term "heterozygous" refers to a genetic condition where the organism or cell has different alleles at corresponding loci on homologous chromosomes.

The term "homozygous" refers to a genetic condition where the organism or cell has identical alleles at corresponding loci on homologous chromosomes.

As used herein, the term "exogenous DNA" or "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

The term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein" (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. A "transformed" cell is thus a cell transfected with a nucleic acid sequence. The term "transformation" refers to the introduction of a nucleic acid (e.g., DNA or RNA) into cells in such a way as to allow expression of the coding portions of the introduced nucleic acid. The term "transgene" refers to an artificial gene which is used to transform a cell of an organism, such as a bacterium or a plant.

The term "genetic marker," as used herein, refers to a nucleotide sequence used to identify different alleles of a gene and/or to locate alleles of a gene on a homologous chromosome in a different species, variety or cultivar. Examples of genetic markers include, but are not limited to, restriction fragment length polymorphisms (RFLP), amplified fragment length polymorphisms (AFLP), single nucleotide polymorphisms (SNPs), microsatellite markers (e.g., SSRs), sequence-characterized amplified region (SCAR) markers, variable number tandem repeats (VNTR), short tandem repeats (STR), cleaved amplified polymorphic sequence (CAPS) markers, and isozyme markers, and similar markers or combinations of such markers that define a specific genetic and chromosomal location.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a variant of a PGR5 protein) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, N.J., 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "tolerant" or "tolerance" refers to the ability of a plant to overcome, completely or to some degree, the detrimental effect of an environmental stress or other limiting factor.

The term "expression" as used herein describes the process undergone by a structural gene to produce a polypeptide. It is a combination of transcription and translation. Expression generally refers to the "expression" of a nucleic acid to produce a polypeptide, but it is also generally acceptable to refer to "expression" of a polypeptide, indicating that the polypeptide is being produced via expression of the corresponding nucleic acid.

As used herein, the term "over-expression" and "up-regulation" refers to the expression of a nucleic acid encoding a polypeptide (e.g., a gene) in a transformed plant cell at higher levels (therefore producing an increased amount of the polypeptide encoded by the gene) than the "wild type" plant cell (e.g., a substantially equivalent cell that is not transfected with the gene) under substantially similar conditions. Thus, to over-express or increase expression of an OMT nucleic acid refers to increasing or inducing the production of the OMT polypeptide encoded by the nucleic acid, which may be done by a variety of approaches, such as increasing the number of genes encoding for the polypeptide, increasing the transcription of the gene (such as by placing the gene under the control of a constitutive promoter), or increasing the translation of the gene, or a combination of these and/or other approaches. Conversely, "under-expression" and "down-regulation" refers to expression of a polynucleotide (e.g., a gene) at lower levels (producing a decreased amount of the polypeptide encoded by the polynucleotide) than in a "wild type" plant cell. As with over-expression, under-expression can occur at different points in the expression pathway, such as by decreasing the number of gene copies encoding for the polypeptide, inhibiting (e.g., decreasing or preventing) transcription and/or translation of the gene (e.g., by the use of antisense nucleotides, suppressors, knockouts, antagonists, etc.), or a combination of such approaches.

As used herein "inhibit" or "inhibiting" expression of a gene indicates that something (e.g., antisense nucleotide, suppressor, antagonist, etc.) acts to reduce or prevent (completely or partially) the transcription, translation and/or other processing step in the expression of a gene, thereby down-regulating the gene expression so that a reduced amount of the active protein encoded by the gene is produced as compared to wild type.

The term "plasmid" as used herein refers to a non-chromosomal double-stranded DNA sequence including an intact "replicon" such that the plasmid is replicated in a host cell.

As used herein, the term "vector" or "expression vector" is used in reference to a vehicle used to introduce an exogenous nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, the term "promoter" or "promoter region" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

The term "operably linked" indicates that the regulatory sequences necessary for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, the term "selectable marker" refers to a gene whose expression allows one to identify cells that have been transformed or transfected with a vector containing the marker gene. For instance, a recombinant nucleic acid may include a selectable marker operably linked to a gene of interest and a promoter, such that expression of the selectable marker indicates the successful transformation of the cell with the gene of interest.

Discussion

The embodiments of the present disclosure encompass isolated nucleotide sequences encoding tomato O-methyltransferase (OMT) genes, isolated peptide sequences for tomato OMT proteins, vectors including a tomato OMT gene, vectors including antisense sequences for an OMT gene, vectors for over-expression of OMT genes, transgenic and introgressed plants and plant cells that under or over-produce guaiacol, and genetic markers to identify variant alleles of tomato OMT genes.

Little is known about how guaiacol is synthesized. Based upon its structure, guaiacol could be synthesized by methylating catechol. This type of reaction is catalyzed by O-methyltransferases (OMTs) that transfer a methyl group from S-adenosyl-L-methionine (AdoMet) to a hydroxyl or carboxyl group on an acceptor molecule (Wang and Pichersky 1999). Many plant OMTs important for phenylpropanoid biosynthesis have been identified. These enzymes synthesize secondary metabolites such as lignin, flavonoids and aromatic molecules (Gang 2005). OMTs with activity on various O-diphenolic substrates, including catechol, have previously been characterized from tobacco and sweet basil (Collendavelloo et al. 1981; Maury et al 1999; Gang et al. 2002). However, activities of such enzymes have only been demonstrated in vitro, and there is no validation of such a function in vivo.

The present disclosure describes and characterizes a tomato catechol OMT (SlOMT1), and its homologs, involved in the synthesis of guaiacol. The examples below demonstrate that this enzyme is able to produce guaiacol from catechol in vitro and that down-regulation and over-expression of SlOMT1 in planta decreases and increases guaiacol emission in fruit, respectively. The in planta data demonstrate that a function of this enzyme and its homologs is to synthesize guaiacol.

As described in Example 1 below, a gene involved in the production of guaiacol was identified in tomato plants. In vitro studies demonstrated that the gene encoded an OMT that catalyzed the production of guaiacol from catechol. The SlOMT1 gene, its homologs, and the encoded protein and homologs from other tomato varieties were isolated and characterized.

The Example also demonstrates that over-expression of this OMT induced higher levels of guaiacol production in vivo, and knockout of endogenous OMT resulted in lower levels of guaiacol production in vivo, relative to wild type plants. Vectors were produced that controlled expression of OMTs in vivo. Thus, in embodiments, vectors can be used to produce transgenic plants that over-express or under-express OMTs in the transgenic plants, thus resulting in transgenic plants that produce different levels of guaiacol than wild-type plants. The methods of the present disclosure can be used to produce new plant varieties that produce tomato fruit with different and/or enhanced flavor.

Furthermore, it was discovered (as discussed in greater detail in Example 2, below) that the sequences for OMT genes are well-conserved in tomato plants, with a *S. lycopersicum* species and a wild relative, *S. pennellii* having about 99% sequence identity at the gene level for the coding sequence (FIG. 8) and about 98% sequence identity for the OMT protein sequences (FIG. 7). This conservation of sequence identity within the *Solanum* genus means that a small number of genetic changes in the sequence may be responsible for differing levels of guaiacol synthesis among various species and varieties of tomato.

The identification of molecular markers for OMT genes, as described in an embodiment in Example 2, enabled identification of OMT genes in other species of tomato. In embodiments of the present disclosure, such molecular markers are used to allow identification of variant alleles of OMT genes that are responsible for higher or lower levels of guaiacol synthesis. Other embodiments of the present disclosure include introgressing these variant alleles into hybrid *S. lycopersicum* plants to produce new plant varieties with different levels of guaiacol content than an ancestor *S. lycopersicum* plant. Such new hybrid varieties can produce fruits with different and improved flavors over the ancestor *S. lycopersicum* tomato fruit.

Isolated Nucleic Acid and Peptide Sequences:

The present disclosure includes isolated nucleotide sequences and peptide sequences corresponding to O-methyltransferases (OMTs) in tomato plants. As described in the Example below, a nucleotide encoding an OMT in *S. lycopersicum* was discovered having a nucleotide sequence of SEQ ID NO: 5, with the coding sequence corresponding to SEQ ID NO: 2. Its homolog in a wild relative *S. pennellii* had SEQ ID. NO: 6, with coding sequence SEQ ID NO: 7, with the coding sequences having about 99% identity (see FIGS. 8A-8T). In an embodiment, the present disclosure includes an isolated DNA molecule, encoding a tomato O-methyltransferase (OMT), with at least 90% sequence identity with SEQ ID NO: 2. In embodiments, the isolated DNA molecules of the present disclosure with at least 90% sequence identity with SEQ ID NO: 2 encode a peptide capable of catalyzing guaiacol from catechol. The cDNA for OMT in *S. lycopersicum* is described in SEQ ID NO: 1. In embodiments, the present disclosure also includes isolated DNA molecules having a sequence chosen from SEQ ID NOs: 1, 2, 5, and 7.

In embodiments, the present disclosure includes isolated peptides having SEQ ID NOs: 3 or 4. SEQ ID NO: 3 is a peptide sequence of an OMT from *S. lycopersicum*, and SEQ ID NO: 4 is a peptide sequence of an OMT from *S. pennellii*. SEQ ID NOs: 3 and 4 have about 98% sequence identity (FIG. 7). In embodiments, the present disclosure also includes isolated peptides having sequences having at least about 90% sequence identity with SEQ ID NOs: 3 and/or 4. In embodiments, such peptides are capable of catalyzing guaiacol from catechol.

The present disclosure also includes fragments of isolated peptides having about 90% sequence identity with SEQ ID NOs: 3 and/or 4. Suitable peptide fragments capable of catalyzing production of guaiacol can be obtained by using appropriate restriction sites using standard methods known to those of skill in the art. An active fragment refers to a continuous portion of the OMT-encoding molecule (e.g., gene) that is less than the entire molecule. Such OMT gene fragments may encode the entire OMT protein or an active fragment and/or functional variant thereof.

In other embodiments, the present disclosure includes isolated antisense polynucleotides that are capable of inhibiting expression of an endogenous tomato OMT gene. The polynucleotides that are capable of inhibiting expression of the OMT gene may inhibit expression directly (e.g., by binding to the OMT mRNA to prevent translation) or via a transcription product (e.g., RNA if the antisense polynucleotide is DNA) of the antisense polynucleotide. Such antisense polynucleotides can be used in vectors to produce knock-out transgenic plant varieties where OMT expression is inhibited or down-regulated, thus reducing guaiacol production in the transgenic plant. In embodiments the antisense polynucleotides of the present disclosure are capable of inhibit expression of an endogenous OMT gene having SEQ ID NO: 2 or having at least 90% sequence identity with SEQ ID NO: 2. In embodiments, when the antisense polynucleotides of the present disclosure are transcribed in a plant, such antisense polynucleotides are able to inhibit expression of an endogenous OMT gene having SEQ ID NO: 2 or having at least 90% sequence identity with SEQ ID NO: 2.

Vectors

Vectors including the DNA molecules described above or antisense nucleotides to the DNA molecules can be useful in producing transgenic plant cells and transgenic plants that express varying levels of OMT. In embodiments, the vectors may include exogenous DNA molecules, such as the OMT genes and fragments described above, or an OMT antisense nucleic acid, such as described above. In embodiments, the exogenous sequence is combined with other regulatory sequences to make a recombinant nucleic acid that can be included in the vector. Additional description of embodiments of vectors including the DNA sequences or antisense sequences described above and regulatory sequences driving the expression of such sequences is provided in the examples below. Additional descriptions of regulatory sequences that may be included in recombinant polynucleotide sequences in embodiments of vectors of the present disclosure are described below.

In embodiments, the present disclosure includes a vector including a DNA molecule encoding a tomato OMT, where the DNA molecule has at least 90% sequence identity with SEQ ID NO: 2, and where the OMT catalyzes production of guaiacol. Such vectors also include at least one regulatory sequence operatively linked to the DNA molecule such that the OMT is expressed in a plant cell into which it is transformed. In embodiments, the regulatory sequence includes a promoter that serves to induce expression of the OMT such that the OMT is over-expressed in a plant cell into which it is transformed relative to a wild type plant cell.

Other embodiments of the present disclosure include a vector including an antisense polynucleotide capable of inhibiting expression an endogenous tomato OMT gene and at least one regulatory sequence operatively linked to the antisense polynucleotide such that the antisense polynucleotide is transcribed in a plant cell into which it is transformed. In embodiments, the antisense polynucleotides may be capable of inhibiting expression of an endogenous OMT gene having SEQ ID NO: 2 or at least 90% sequence identity with SEQ ID NO: 2.

Transgenic Plants

The polynucleotide sequences and vectors described above can be used to produce transgenic plant cells and transgenic plants. The present disclosure includes plants including recombinant polynucleotides including the DNA molecules encoding the tomato OMTs and antisense polynucleotides described above. Also encompassed by the present disclosure are transgenic plants transformed with vectors including the nucleotide sequences described above, the antisense polynucleotides described above, and/or fragments of the nucleic acids encoding the OMT proteins of the present disclosure.

In embodiments the present disclosure includes a tomato plant including a plurality of cells (e.g., more than one or two cells of the plant, but which may be all or less than all the cells of the plant), including a recombinant polynucleotide of the present disclosure. In embodiments, the recombinant polynucleotide includes a DNA molecule encoding a tomato OMT and at least one regulatory sequence operatively linked to the DNA molecule such that the OMT is expressed in the plant cell. In embodiments, the tomato plant has increased expression of O-methyltransferase (OMT) relative to a wild type plant. In some embodiments of such plants of the present disclosure the DNA molecule has at least 90% sequence identity with SEQ ID NO: 2, and the OMT catalyzes production of guaiacol. In other embodiments, the DNA molecule has SEQ ID NO: 2 or SEQ ID NO: 7.

Similarly, embodiments of the present disclosure also include tomato plants including a plurality of cells, where the cells include a recombinant polynucleotide including an antisense polynucleotide and at least one regulatory sequence operatively linked to the antisense polynucleotide such that the antisense polynucleotide is transcribed in the plant cell. The antisense polynucleotide is capable of inhibiting expression of an endogenous tomato O-methyltransferase (OMT) gene having at least 90% sequence identity with SEQ ID NO: 2. In such embodiments, the tomato plant has decreased expression of O-methyltransferase (OMT) relative to a wild type plant In embodiments, non-essential nucleotides can be placed at the 5' and/or 3' end of the DNA molecules encoding OMT peptides or the antisense polynucleotides without affecting the functional properties of the molecule. For example, the nucleotides encoding the OMT polypeptide may be conjugated to a nucleic acid encoding a signal or transit (or leader) sequence at the N-terminal end (for example) of the OMT polypeptide that co-translationally or post-translationally directs transfer of the OMT polypeptide. The nucleotide sequence may also be altered so that the encoded OMT polypeptide is conjugated to a linker, selectable marker, or other sequence for ease of synthesis, purification, and/or identification of the protein.

A transformed plant cell of the present disclosure can be produced by introducing into a plant cell a vector that includes a recombinant nucleic acid molecule described above. In embodiments, the recombinant nucleic acid molecule encodes an exogenous OMT protein or active fragment thereof or antisense polynucleotide capable of inhibiting expression of an endogenous OMT. As described above, the recombinant nucleic acid molecule of the vector and/or transformed plant cell also includes at least one regulatory sequence operatively linked to the DNA molecule encoding the OMT protein or fragment or the antisense polynucleotide. When the vector is transformed into a plant cell, the exogenous OMT gene, fragment or antisense polynucleotide is expressed in the transformed cell. Depending on the DNA molecule included in the vector, expression may increase or decrease the production of OMT and thereby increase or decrease production of guaiacol in the cell. In an embodiment, tomato plants of the present disclosure can be grown from a transgenic tomato plant cell transformed with the vectors according to the present disclosure described above (e.g., including a DNA molecule encoding a tomato OMT and having at least 90% sequence identity with SEQ ID NO: 2 and including at least one regulatory sequence operatively linked to the DNA molecule).

Techniques for transforming a wide variety of plant cells are well known in the art and described in the technical and scientific literature. See, for example, Weising et al. (1988) Ann. Rev. Genet. 22:421-477. To express an exogenous OMT gene or fragment thereof or antisense nucleotide in a plant cell, the exogenous nucleotide can be combined (e.g., in a vector) with transcriptional and/or translational initiation regulatory sequences that direct the transcription of the gene and/or translation of the encoded protein in the plant cell.

For example, for over-expression, a constitutive plant promoter may be employed. A "constitutive" promoter is active under most environmental conditions and states of cell differentiation. Examples of constitutive promoters include the cauliflower mosaic virus (CaMV) 35S transcription initiation region, the 1'- or 2'-promoter derived from T-DNA of *Agrobacterium tumefaciens*, the ACT11 and Cat3 promoters from *Arabidopsis* (Huang et al. (1996) Plant Mol. Biol. 33:125-139 and Zhong et al. (1996) Mol. Gen. Genet. 251:196-203), the stearoyl-acyl carrier protein desaturase gene promoter from *Brassica napus* (Solocombe et al. (1994) Plant Physiol. 104: 1167-1176), and the GPc 1 and Gpc2 promoters from maize (Martinez et al. (1989) J. Mol. Biol. 208:551-565 and Manjunath et al. (1997) Plant Mol. Biol. 33:97-112).

Alternatively, a plant promoter may be employed to direct expression of the exogenous nucleic acid in a specific cell type (e.g., tissue-specific promoters) or under more precise environmental or developmental control (e.g., inducible promoters). Examples of environmental conditions that may affect transcription by inducible promoters include anaerobic conditions, elevated temperature, the presence of light, contact with chemicals or hormones, or infection by a pathogen. Examples of such promoters include the root-specific ANR1 promoter (Zhang and Forde (1998) Science 279:407), the photosynthetic organ-specific RBCS promoter (Khoudi et al. (1997) Gene 197:343) and the tomato fruit ripening-specific E8 promoter (Deikman J, Kline R, Fischer R L. 1992Organization of Ripening and Ethylene Regulatory Regions in a Fruit-Specific Promoter from Tomato (Lycopersicon-Esculentum). Plant Physiology 100: 2013-2017).

For proper polypeptide expression, a polyadenylation region at the 3'-end of the coding region can be included. The polyadenylation region can be derived from the natural gene, from a variety of other plant genes, or from T-DNA.

A selectable marker can also be included in the recombinant nucleic acid to confer a selectable phenotype on plant cells. For example, the selectable marker may encode a protein that confers biocide resistance, antibiotic resistance (e.g., resistance to kanamycin, G418, bleomycin, hygromycin), or herbicide resistance (e.g., resistance to chlorosulfuron or Basta). Thus, the presence of the selectable phenotype indicates the successful transformation of the host cell. An exemplary selectable marker includes the beta-glucuronidase (GUS) reporter gene.

A recombinant nucleic acid that encodes an exogenous OMT gene or antisense polynucleotide of the present disclosure may be introduced into the genome of a desired plant host cell by a variety of conventional techniques. The recombinant nucleic acid including the exogenous nucleic acid and one or more of the additional elements described above (e.g., promoter, selectable marker, etc.) may be incorporated into a vector or a plasmid for use in introducing the recombinant nucleic acid to the plant cell. Various plasmids and methods of use are known in the art and described in the literature.

Then, other techniques may be employed for introducing a plasmid or naked recombinant nucleic acid into the plant cell to be transformed. For example, the recombinant nucleic acid may be introduced directly into the genomic DNA of a plant cell using techniques such as, but not limited to, electroporation and microinjection of plant cell protoplasts, or the recombinant nucleic acid can be introduced directly to plant tissue using ballistic methods, such as DNA particle bombardment.

Microinjection techniques are known in the art and well described in the scientific and patent literature. The introduction of a recombinant nucleic acid using polyethylene glycol precipitation is described in Paszkowski et al. (1984) EMBO J. 3:2717-2722. Electroporation techniques are described in Fromm et al. (1985) Proc. Natl. Acad. Sci. USA 82:5824. Ballistic transformation techniques are described in Klein et al. (1987) Nature 327:70-73.

The recombinant nucleic acid may also be combined with suitable T-DNA flanking regions and introduced into a conventional *Agrobacterium tumefaciens* host vector, or other suitable vector. The virulence functions of the *Agrobacterium tumefaciens* host will direct the insertion of the recombinant nucleic acid including the exogenous nucleic acid and adjacent marker into the plant cell DNA when the cell is infected by the bacteria. *Agrobacterium tumefaciens*-mediated transformation techniques, including disarming and use of binary vectors, are known to those of skill in the art and are well described in the scientific literature. See, for example, Horsch et al. (1984) Science 233:496-498; Fraley et al. (1983) Proc. Natl. Acad. Sci. USA 80:4803; and Gene Transfer to Plants, Potrykus, ed., Springer-Verlag, Berlin, 1995.

A further method for introduction of the recombinant nucleic acid into a plant cell is by transformation of plant cell protoplasts (stable or transient). Plant protoplasts are enclosed only by a plasma membrane and will therefore more readily take up macromolecules like exogenous DNA. These engineered protoplasts can be capable of regenerating whole plants. Suitable methods for introducing exogenous DNA into plant cell protoplasts include electroporation and polyethylene glycol (PEG) transformation. As used herein, "electroporation" is a transformation method in which a high concentration of plasmid DNA (containing exogenous DNA) is added to a suspension of host cell protoplasts, and the mixture shocked with an electrical field of about 200 to 600 V/cm. Following electroporation, transformed cells are identified by growth on appropriate medium containing a selective agent.

The presence and copy number of the exogenous nucleic acid in a transgenic plant can be determined using methods well known in the art, e.g., Southern blotting analysis. Expression of the exogenous OMT nucleic acid or antisense nucleic acid in a transgenic plant may be confirmed by detecting an increase or decrease of mRNA or the OMT polypeptide in the transgenic plant. Methods for detecting and quantifying mRNA or proteins are well known in the art.

Transformed plant cells that are derived by any of the above transformation techniques, or other techniques now known or later developed, can be cultured to regenerate a whole plant. In embodiments, such regeneration techniques may rely on manipulation of certain phytohormones in a tissue culture growth medium, typically relying on a biocide or herbicide selectable marker that has been introduced together with the exogenous nucleic acid. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. (1987) Ann. Rev. Plant Phys. 38:467-486. Once the exogenous OMT nucleic acid or antisense nucleic acid has been confirmed to be stably incorporated in the genome of a transgenic plant, it can be introduced into other plants by sexual crossing. Any of a number of standard breeding techniques can be used, depending upon the species to be crossed.

The present disclosure also includes methods of increasing or decreasing/inhibiting the expression of OMT in tomato plants relative to a wild type plant of the same variety. An embodiment for increasing the expression of OMT in a tomato plant involves integrating into the genome of at least one cell of the plant a DNA molecule encoding a tomato OMT that catalyzes production of guaiacol and at least one regulatory sequence operatively linked to the DNA molecule such that the OMT is expressed in the plant cell. In embodiments, the OMT may have at least 90% sequence identity with SEQ ID NO: 2, such as the sequences described above. When the plant is grown, the OMT is over-expressed relative to a wild type plant cell. Such plants can produce more guaiacol than a corresponding wild-type plant. An embodiment for inhibiting expression of endogenous OMT in a tomato plant involves integrating into the genome of at least one cell of the plant an antisense polynucleotide capable of inhibiting expression of an endogenous OMT gene and at least one regulatory sequence operatively linked to the antisense polynucleotide, such that it is transcribed in the cell. When the plant is grown, the antisense polynucleotide inhibits expression of the tomato OMT so that the plant produces less guaiacol than a corresponding wild-type plant.

Genetic Markers

The present disclosure also includes genetic markers useful for identifying different alleles of the OMT gene in other tomato varieties and species. In embodiments, such markers may include, but are not limited to restriction fragment length polymorphisms (RFLP), amplified fragment length polymorphisms (AFLP), single nucleotide polymorphisms (SNPs), microsatellite markers (e.g., SSRs), sequence-characterized amplified region (SCAR) markers, variable number tandem repeats (VNTR), short tandem repeats (STR), cleaved amplified polymorphic sequence (CAPS) markers, and isozyme markers, and similar markers or combinations of such markers for the OMT gene.

In embodiments, the present disclosure includes an OMT marker having SEQ ID NO: 8 and/or SEQ ID NO: 9 (FIG. 9). Such markers were used to identify alleles of the OMT gene in a wild relative of the domestic tomato, S. pennellii, which produces higher levels of guaiacol than S. lycopersicum.

Introgression Lines

In embodiments of the present disclosure, variant alleles of the OMT gene can be discovered with use of the genetic markers of the present disclosure described above. These variant alleles can then be characterized, and the alleles responsible for various traits can be identified. In embodiments of the present disclosure, new hybrid tomato lines with desirable traits can be obtained by introgressing alleles responsible for those traits into hybrid S. lycopersicum plants, as described in more detail below. Embodiments of the present disclosure include identifying alleles responsible for different (e.g., higher or lower) levels of guaiacol synthesis (relative to a wild type S. lycopersicum variety, such as the M82 described in the present disclosure). Then, the alleles for a desired level of guaiacol synthesis can be introgressed into a parent S. lycopersicum plant, to produce a new hybrid line with higher or lower levels of guaiacol synthesis than the parent line. Thus, in embodiments of the present disclosure, introgression can be used to produce new plant varieties with different levels of guaiacol content than an ancestor S. lycopersicum plant. As described in the examples below, a new S. lycopersicum line with introgressed alleles from S. pennellii was produced with higher levels of guaiacol synthesis than the parent S. lycopersicum ancestor line. Such new hybrid varieties can produce fruits with different and/or improved flavors over the ancestor S. lycopersicum tomato fruit.

The identification of a O-methyltransferase gene from a species of tomato plant allows the preparation and use of specific molecular markers, such as those disclosed herein, in a plant breeding program to identify and introgress an OMT gene conferring an altered guaiacol production phenotype to agronomically elite tomato lines. It also allows movement of the trait within agronomically elite tomato lines. Marker-assisted introgression involves the transfer of a chromosomal region, by tracking one or more markers, from one germplasm to a second germplasm. The basic principle for association is that the closer together two features are on a chromosome, the more likely they are to be inherited together. Briefly, a cross is made between two genetically compatible but divergent parents relative to a trait under study (e.g. an O-methyltransferase (OMT) gene conferring an altered guaiacol production phenotype). Morphological, genetic or molecular markers are then used to follow the segregation of the trait under study in the progeny from a cross. As described in the present disclosure, a chromosomal region was identified that is responsible for altered guaiacol production, and markers were designed from this region to assist breeding to introgress this chromosomal region into other tomato germplasm that lacks a particular OMT gene conferring an altered guaiacol production phenotype.

Introgression of a particular chromosomal region or set of regions into a plant genotype is defined, for example, as the result of the process of backcross conversion. Additional examples of breeding techniques intended to reach the same result include pedigree selection and dihaploidization of an F1. A plant genotype into which a DNA sequence has been introgressed may be referred to as a converted genotype, line, or variety. Such genotype, line, or variety may be an inbred or a hybrid genotype, line, or variety. Similarly a plant genotype lacking said desired DNA sequence may be referred to as an unconverted genotype, line, or variety. During breeding, the genetic markers linked to an OMT gene conferring an altered guaiacol production phenotype may be used to assist in breeding for the purpose of producing tomato plants with altered guaiacol production. Localization of such markers to specific genomic regions further allows for use of associated sequences in breeding and to develop additional linked genetic markers. It will be understood to those of skill in the art that other markers or probes which also map to the chromosomal region as identified herein could be employed to identify plants comprising a desired O-methyltransferase phenotype. The chromosomal region discussed in the present disclosure facilitates introgression of an OMT gene, or gene fragment, conferring an altered guaiacol production phenotype, into other germplasm, preferably agronomically useful tomato germplasm. Linkage blocks of various sizes could be transferred within the scope of this disclosure as long as the chromosomal region contains an O-methyltransferase (OMT) gene or fragment and alters guaiacol production of an agronomically desirable tomato plant, line, or variety. Accordingly, the methods of the present disclosure may be practiced using any molecular markers that are associated with the identified region, provided that the markers are polymorphic between the parents in a population.

Representative Embodiments

The following represent some additional, non-exclusive embodiments of the present disclosure discussed above and described in the examples below. Those of skill in the art will be able to appreciate variations to the following embodiments that are also within the scope of the present disclosure.

In an embodiment, the present disclosure includes an isolated DNA molecule encoding a tomato O-methyltransferase (OMT), wherein the DNA molecule has at least 90% sequence identity with SEQ ID NO: 2, and wherein the OMT catalyzes production of guaiacol. In an embodiment, the isolated DNA molecule comprises SEQ ID NO: 2. In another embodiment, the isolated DNA molecule comprises SEQ ID NO: 7.

In an embodiment, the present disclosure includes an isolated DNA molecule encoding a tomato O-methyltransferase (OMT), wherein the DNA molecule comprises SEQ ID NO: 2.

In an embodiment, the present disclosure includes an isolated peptide comprising SEQ ID NO: 3

In an embodiment, the present disclosure includes an isolated peptide having at least 90% sequence identity with SEQ ID NO: 3. In an embodiment, the isolated peptide comprises SEQ ID NO: 3. In an embodiment, the isolated peptide comprises SEQ ID NO: 4.

In an embodiment, the present disclosure includes a vector comprising a DNA molecule encoding: a tomato O-methyltransferase (OMT), wherein the DNA molecule has at least 90% sequence identity with SEQ ID NO: 2, and wherein the OMT catalyzes production of guaiacol; and at least one regulatory sequence operatively linked to the DNA molecule such that the OMT is expressed in a plant cell into which it is transformed. In an embodiment of the vector, the regulatory sequence comprises a promoter that serves to induce expression of the OMT such that the OMT is over-expressed in a plant cell into which it is transformed relative to a wild type plant cell.

In an embodiment, the present disclosure includes a transgenic tomato plant cell transformed with the vector described above. An embodiment includes a transgenic tomato plant comprising the plant cells described herein. An embodiment also includes the transgenic tomato plant of the present disclosure, wherein the plant produces fruit that comprises more guaiacol than a fruit from a wild type plant of the same variety as the transgenic plant.

In an embodiment, the present disclosure includes a method for increasing the expression of endogenous O-methyltransferase (OMT) in a tomato plant, relative to a wild type plant, comprising: integrating into the genome of at least one cell of the plant the vector described above; growing said plant, whereby said OMT is over-expressed relative to a wild type plant cell. In an embodiment of such methods, the over-expression results in production of fruit that comprises more guaiacol as compared to a fruit from a wild type plant.

In an embodiment, the present disclosure includes an isolated antisense polynucleotide, wherein the antisense polynucleotide is capable of inhibiting expression of an endogenous tomato O-methyltransferase (OMT) gene comprising SEQ ID NO: 2.

In an embodiment, the present disclosure includes an isolated antisense polynucleotide, wherein the antisense polynucleotide is capable of inhibiting expression of an endogenous tomato O-methyltransferase (OMT) gene having at least 90% sequence identity with SEQ ID NO: 2.

In an embodiment, the present disclosure includes a vector comprising: an antisense polynucleotide capable of inhibiting expression of an endogenous tomato O-methyltransferase (OMT) gene having at least 90% sequence identity with SEQ ID NO: 2, and at least one regulatory sequence operatively linked to the antisense polynucleotide such that the antisense polynucleotide is transcribed in a plant cell into which it is transformed.

In an embodiment, the present disclosure includes a transgenic tomato plant cell transformed with the vector described immediately above. In an embodiment, the present disclosure also includes a transgenic tomato plant grown from the plant cell above. In an embodiment the transgenic tomato plant produces fruit that comprises less guaiacol than a fruit from a wild type plant of the same variety as the transgenic plant.

In an embodiment, the present disclosure includes a method for inhibiting the expression of endogenous O-methyltransferase (OMT) in a tomato plant comprising: integrating into the genome of at least one cell of the plant the vector including the antisense polynucleotide described above; and growing said plant, whereby said antisense polynucleotide inhibits expression of the tomato O-methyltransferase (OMT) gene. In an embodiment of such methods, the inhibition of expression results in production of fruit that comprises less guaiacol as compared to a fruit from a wild type plant.

In an embodiment, the present disclosure includes a genetic marker capable of identifying a DNA molecule encoding tomato O-methyltransferase (OMT) having at least 90% sequence identity to SEQ ID NO: 2. In an embodiment, the genetic marker has a forward sequence comprising SEQ ID NO: 8. In an embodiment, the genetic marker has a reverse sequence comprising SEQ ID NO: 9. In an embodiment, the marker is capable of identifying alleles of the O-methyltransferase (OMT) gene in a plurality of varieties of tomato plant.

In an embodiment, the present disclosure includes an isolated DNA molecule encoding a tomato O-methyltransferase (OMT), wherein the DNA molecule has at least 90% sequence identity with SEQ ID NO: 2, wherein tomato plants having the endogenous DNA molecule encoding for the OMT produce less guaiacol than plants having the endogenous DNA molecule of SEQ ID NO: 2. In an embodiment, the isolated DNA molecule comprises SEQ ID NO: 7.

In an embodiment, the present disclosure includes a method for altering the production of guaiacol in a tomato plant, comprising: identifying a first tomato plant variety that produces fruit with desired levels of guaiacol as compared to a second tomato plant variety; identifying a genetic marker associated with an O-methyltransferase (OMT) gene from the first plant variety that is responsible for the altered guaiacol production; and monitoring the marker genotype during breeding with the second tomato plant variety to select for introgression of a genomic fragment responsible for the altered guaiacol production phenotype into the genome of the second tomato plant to produce a new line of tomato plants that produce fruit with altered levels of guaiacol as compared to the second tomato plant variety. In an embodiment of the method, the first tomato plant variety produces fruit with lower levels of guaiacol as compared to the second tomato plant variety.

In an embodiment, the present disclosure includes a hybrid *Solanum lycopersicum* plant having as one of its ancestors a parental *S. lycopersicum* plant, wherein the hybrid *S. lycopersicum* plant has a genome comprising at least one allele of an O-methyltransferase (OMT) gene associated with lower guaiacol production than in the parental *S. lycopersicum* plant, wherein the allele has been introgressed into the genome of the hybrid *S. lycopersicum* plant from a second *Solanum* species, and wherein the hybrid *S. lycopersicum* produces fruit having lower levels of guaiacol than the fruit produced by a plant from the parental *S. lycopersicum* variety. In an embodiment of the hybrid *Solanum lycopersicum* plant the second *Solanum* species is *Solanum penneffii*.

Additional details regarding the isolated nucleotide and peptide sequences, vectors, genetic markers, transgenic and introgressed plants and methods of making the transgenic and/or introgressed tomato plants of the present disclosure can be found in the Examples below.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the numerical value and the measurement technique.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

O-methyltransferases (OMT) are important enzymes in the biosynthesis of many small molecules, such as, lignin monomers, flavonoids, alkaloids, and aroma compounds. The present example demonstrates that tomato OMTs are involved in the biosynthesis of guaiacol, a small volatile molecule with a smoky aroma that contributes to tomato flavor. Although thought to be correlated with tomato liking, little is known about how this compound is synthesized. One possible route for synthesis is via catechol methylation. The present disclosure describes a tomato O-methyltransferase (SlOMT1) with homology to a *Nicotiana tabacum* catechol OMT. SlOMT1 was cloned from *Solanum lycopersicum* (cv. M82) and expressed in *E. coli*. The recombinant SlOMT1 enzyme preferentially methylated catechol, producing guaiacol. Slight activity was also observed on orcinol and caffeic acid. To verify the in vivo function of SlOMT1, gene expression was both decreased and increased in *S. lycopersicum* cv. Flora-Dade. Knockdown of SlOMT1 resulted in reduction of guaiacol in fruit, while fruit in which SlOMT1 was over-expressed had increased guaiacol emission. However, it was suspected that catechol availability might limit guaiacol production in S/OMT1 over-expressors, as normal endogenous levels of catechol are low. To test this hypothesis, WT and SlOMT1 over-expressing tomato pericarp discs were supplied with exogenously applied catechol. Guaiacol production increased in both WT and transgenic fruit discs, although to a greater extent in SlOMT1 over-expressing discs. The results of this study demonstrate that SlOMT1 is a catechol-O-methyltransferase that functions to produce guaiacol in tomato fruit.

Materials and Methods
Protein Purification and Expression

SGN-U582403 (SlOMT1) was PCR-amplified from fruit cDNA from *Solanum lycopersicum*. The product was cloned into vector pENTR/D/TOPO and sequenced (CHUL Research Center, Quebec, Canada). The coding regions were then cloned into vector pET160 containing a His-tag (Invitrogen) by recombination and transformed into *E. coli* BL21-DE3 (Invitrogen) for inducible protein expression. Bacteria were precultured 16 hr at 37° in Luria-Bertani broth containing 50 µg/mL carbenicillin, the culture was used to inoculate 100 mL of the same medium. Cells were grown at 24° to an $OD_{600}$ of 0.5. Protein expression was induced by adding isopropyl-1-β-D-thiogalactoside to the medium at a final concentration of 0.1 mM. Induced cultures continued growing at 25° for 16 hr.

Cells were harvested by centrifugation (10 min, 5000 rpm) and resuspended in 6 mL of lysis buffer (1×PBS, lysozyme, 10% v/v glycerol, and Bacterial Protease Inhibitor Cocktail [Sigma, http://www.sigmaaldrich.com/]) and lysed with sonication. Protein was purified using Ni-Talon® (Clonetech) affinity chromatography. The column was washed with 1×PBS containing 5 mM imidazole. Imidazole concentration was increased to 150 mM in the elution buffer. Protein levels were quantified using Bradford Reagent (Bio-Rad, http://www.bio-rad.com/). Protein was stored in 16% glycerol at −80° C.

Enzymatic Assay

For substrate specificity assays, 5 µL purified enzyme was assayed at 25° in a 100 µL reaction containing 50 mM Tris-HCl, pH 7.5, 100 mM KCl, 2.8 mM BME, 15 µM substrate, 10 mM SAM, 0.4 mM [methyl-$^{14}$C] AdoMet (specific activity 50.4 mCi mmol$^{-1}$; Amersham). Substrates were diluted in 50% EtOH. Assays were done in triplicate, including boiled enzyme controls. After 30 min at 25° the reactions were stopped by adding equal volumes of hexanes. The methylated substrate was extracted on a vortex mixer for 15 sec and centrifuging at 13 200 g for 5 min. 50 µL of the organic layer was counted for 10 min in 3 ml Ready Gel Scintillation Fluid (Beckman Coulter, http://www.beckmancoulter.com). Counts for the boiled enzyme controls were subtracted from the sample counts, and activity for catechol was normalized to 100%. For the $K_m$ of catechol, procedures were the same as above, except for catechol concentrations. Concentrations used were: 0, 1, 5, 15, 25, and 50 µM.

Production of Transgenic Plants

The full-length open reading frame of SlOMT1 was cloned into a vector, pHKoe, containing the constitutive FMV 35S promoter (Richins et al., 1987) for over-expression. *Solanum lycopersicum* (Flora-Dade) cotyledons were transformed by *Agrobacterium*-mediated transformation (McCormick et al., 1986) with the kanamycin selectable marker, NPTII. Anti-sense constructions were made by cloning SlOMT1 into pK2WG7 (Karimi et al. 2002). The Plant Transformation Core Research Facility at the University of Nebraska transformed the construct into Flora-Dade.

Volatile Collection

Volatiles were collected from tomato fruits according to Tieman et al. (2006). Briefly, air was passed over the samples and volatiles were collected on a SuperQ Resin for 1 h. Five µL of nonyl acetate were added to each column as an internal control. Volatiles were eluted off the column with methylene chloride and run on a GC/MS and GC for analysis as described in Tieman et al. (2006).

Quantitative RT-PCR

Tomato fruit was chopped and quickly frozen in liquid nitrogen. Samples were stored at −80° until further use. RNA was extracted using Qiagen Plant RNeasy kit. Possible genomic DNA contamination was removed by on column DNaseI treatment for 15 min at room temperature. Quantitative PCR was performed with StepOnePlus™ Real-Time PCR System (Applied Biosystems) using total amount of 325 ng total RNA, Taqman® 1-step kit (Applied Biosystems), 500 nm forward and reverse primer. A total reaction volume of 25

µl was used. A standard curve was generated using pENTR-OMT1 ranging from $10^5$ to $10^{10}$ copies per 5 µL.

Catechol Feeding

Tomato discs were cut from pericarp tissue of ripe WT and SlOMT1 over-expressing fruit using a size 10 borer. A hundred discs were used for each sample treatment. Discs were placed in petri dishes and an X was cut in the top of each. 10 µl of either water or 1 M catechol dissolved in water was pipetted into each disc. Cover were place on petri dish and disc were left to incubate for 5 hr. Disc were then place in glass tube and volatiles were extracted as previously described. Guaiacol was quantified on GC/MS using a guaiacol standard curve.

Results

Identifying a Catechol-O-Methyltransferase from *S. lycopersicum*

Potential *S. lycopersicum* catechol OMT candidates were selected by identification of genes with homology to previously characterized catechol and caffeic acid OMTs (FIG. 1). Five candidate genes were selected, SGN-U582403, SGN-U565623, SGN-U319245, SGN-U575022, and SGN-U321686. Full length cDNAs were synthesized from *S. lycopersicum* cv. M82 ripe fruit RNA. Candidate genes were cloned into pET160 plasmids for expression in *E. coli*. Initial screens were performed by adding catechol directly to bacterial cultures expressing induced protein and measuring guaiacol production. Only one of the five candidates, U582403, converted catechol to guaiacol.

Specific Activity of SlOMT1

Figure 2:
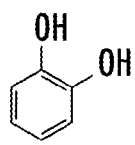
FIG. 2 illustrates the chemical structure and relative activity of SlOMT1 on catechol and substrates with similar structure to catechol. Relative activity was determined by incubating purified SlOMT with excess amounts of $[C^{14}]$-AdoMet and 15 nM of substrate. Products were extracted with hexanes and measured with a scintillation counter. Relative activity is expressed as a percentage of activity on catechol. 1=catechol; 2=guaiacol; 3=salicylic acid; 4=benzoic acid; 5=orcinol; 6=caffeic acid.
Figure 2:
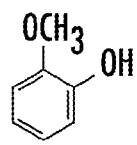
Figure 2:
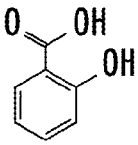
Figure 2:
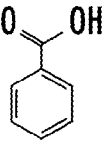
Figure 2:
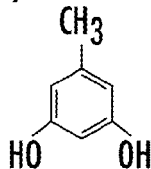
Figure 2:
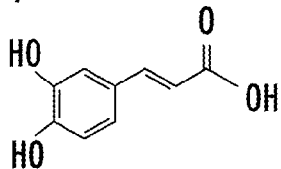

To further test the specificity of SGN-U582403 (SlOMT1) for catechol, the activity of SlOMT1 on substrates with similar structure to catechol was measured. Purified protein was incubated with [$^{14}$C]-AdoMet and the following potential substrates: catechol, guaiacol, salicylic acid, benzoic acid, orcinol, or caffeic acid. Products were extracted with hexanes and measured with a scintillation counter. SlOMT1 only had slight activity on orcinol and caffeic acid as compared to catechol (FIG. 2).

Figures 3A, 3B:
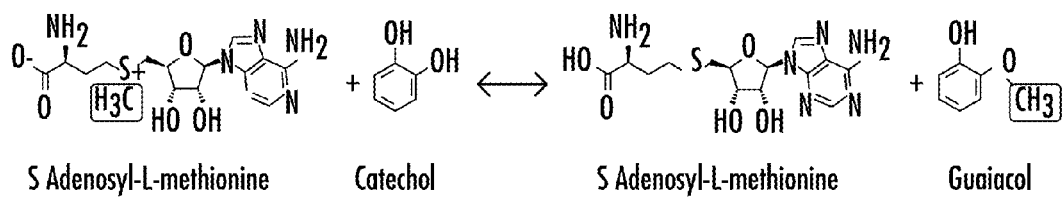
FIG. 3A illustrates the predicted pathway for the synthesis of guaiacol from catechol.
FIG. 3B shows the specific activity and turnover rate of SlOMT1. Values were determined using non-linear regression.

To test the specific activity of the affinity of SlOMT1 for catechol, recombinant enzyme was purified from *E. coli*. Enzyme assay were conducted by incubating purified protein with excess amounts of [$^{14}$C]-AdoMet and various amounts of catechol. The $K_m$ and Kcat values were determined (FIG. 3). Guaiacol was confirmed as the product formed by GC-MS.

Characterization of SlOMT1 in Planta

Figure 4A:
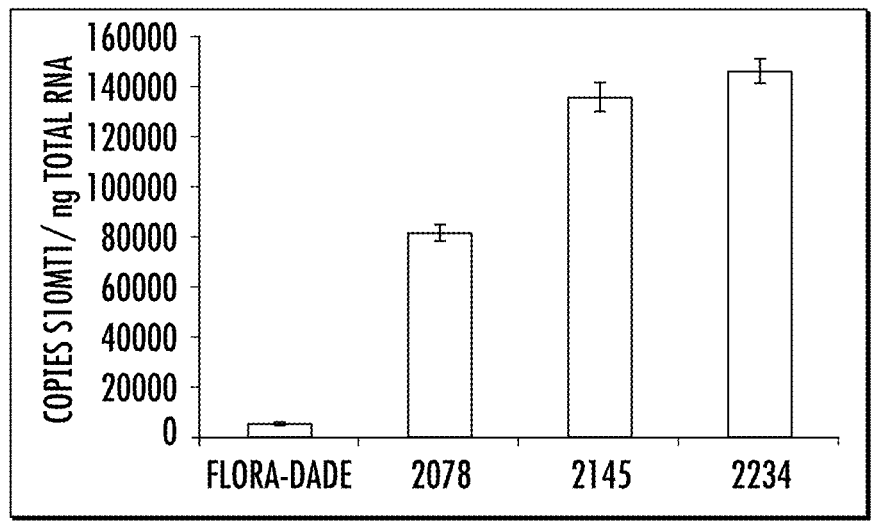
FIGS. 4A-4B are bar graphs illustrating gene expression level in transgenic plants.
Figure 5A:
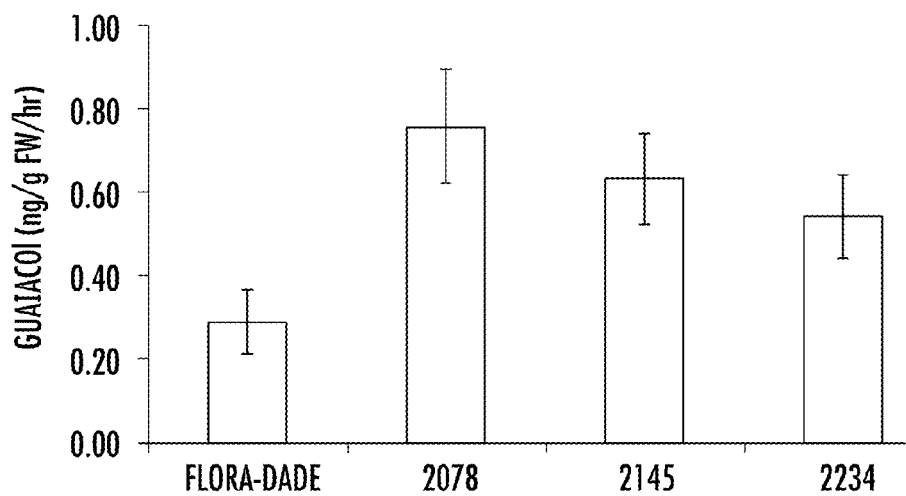
FIGS. 5A-5B are bar graphs illustrating guaiacol levels emitted from transgenic fruit. Three lines over-expressing SlOMT1 are shown in FIG. 4A.

To confirm that SlOMT1 is an important enzyme in guaiacol synthesis, SlOMT1 was cloned into a vector for constitutive over-expression in planta. The construct was transformed into *S. lycopersicum* cv. Flora-Dade using *Agrobacterium*-mediated transformation (McCormick et al., 1986). Seventeen independent lines were initially screened for transgene expression. Gene expression levels were assessed by quantifying SlOMT1 mRNA levels using TaqMan® qPCR (FIG. 4A), with the over-expression lines producing higher SlOMT1 mRNA levels. Eight of these lines were screened for over-expression of the SlOMT RNA. Based on this screen, three lines were subsequently analyzed for guaiacol synthesis in ripe fruits. Volatiles were collected from fruit (FIG. 5A). Increases in guaiacol emission were observed in lines over-expressing SlOMT1. Guaiacol production was increased from WT level.

Figure 4B:
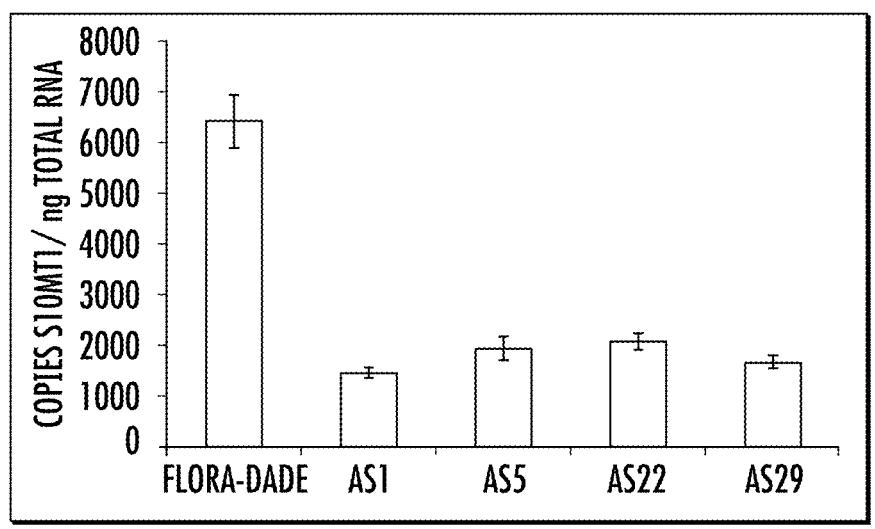
Figure 5B:
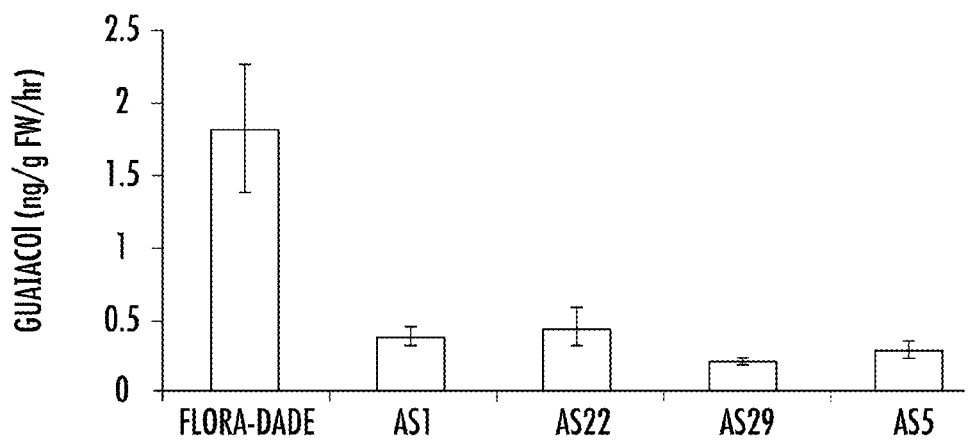

SlOMT1 was also cloned into pK2WG7 (Karimi et al. 2002) for antisense knock-down and transformed into cv. Flora-Dade. Twenty-five lines were initially screened for knockdown of SlOMT1 RNA using leaf tissue. The four best lines were then further screen for SlOMT1 mRNA levels in fruit using TaqMan® qPCR (FIG. 4B). Volatiles were collected from ripe fruit (FIG. 5B). Reduction in SlOMT1 mRNA levels and in guaiacol emission was observed in knock-down lines including the SlOMT antisense polynucleotide.

Disc Feeding with Catechol

Figures 6A, 6B:
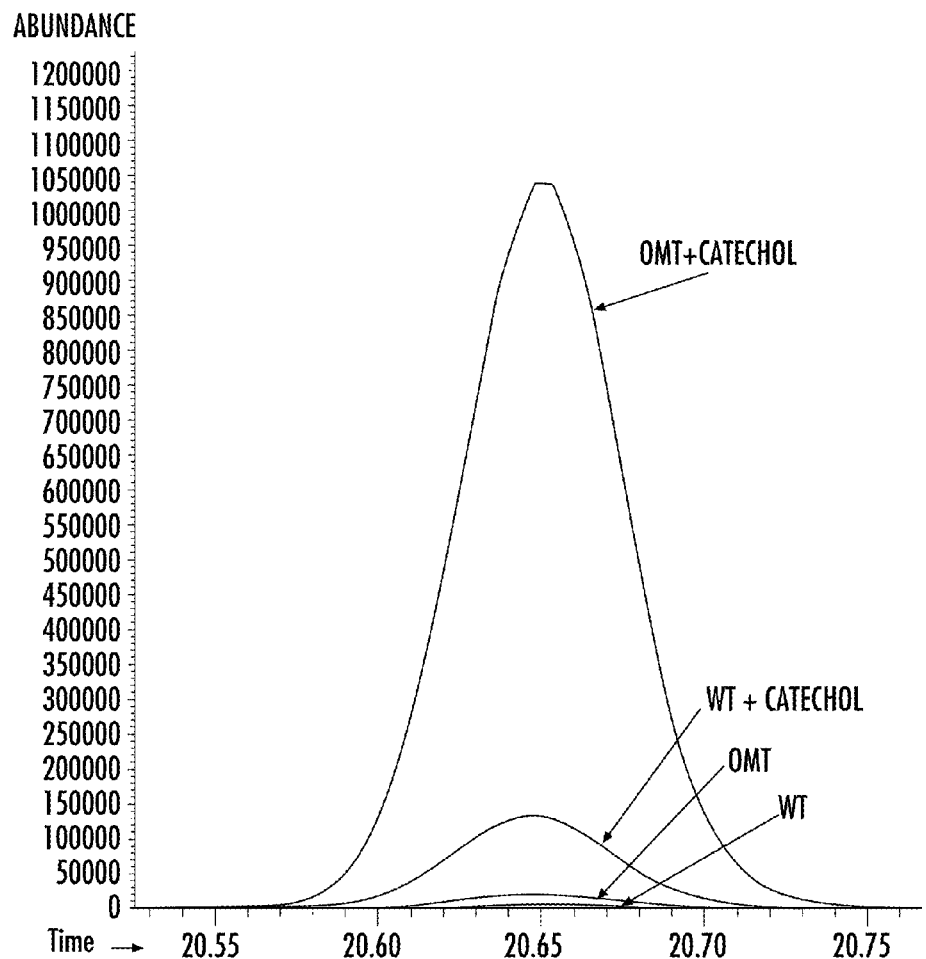
FIGS. 6A and 6B illustrate results of catechol feeding of tomato discs. Tomato fruit discs were made from the pericarp of Flora-Dade and SlOMT1$_{OE}$ ripe fruit and treated with water or catechol. Volatiles of the discs were collected after 5 h and analyzed using GC-MS.

While knock-down lines effectively reduced synthesis of guaiacol, over-expression of SlOMT had much less effect on guaiacol levels. These results suggest that while SlOMT is essential for guaiacol synthesis, it may not be rate-limiting under normal circumstances. Rather, low concentrations of catechol might limit the production of guaiacol in SlOMT1 plants. Thus, to further test this, catechol was fed to fruit pericarp discs of Flora-Dade (WT) and SlOMT1 over-expressing lines. Volatiles were collected after incubation for four hours. Both WT and SlOMT1 discs produced increased guaiacol when fed catechol. However, WT discs produced 36 times as much guaiacol as the unfed control, while SlOMT1 discs produced 52 times as much guaiacol as the unfed control (FIG. 6). These results indicate that while SlOMT catalyzes the conversion of catechol to guaiacol, the availability of catechol likely limits guaiacol synthesis in fruit tissue.

Discussion

Although little is known about how guaiacol is synthesized in tomato fruits or any plant, the present inventors tested whether guaiacol could be made by the methylation of catechol by an OMT. A potential candidate gene was identified by finding homologs of previously characterized caffeic acid and catechol OMTs. Of the five candidate *S. lycopersicum* genes that were screened for catechol activity, only SlOMT1 was capable of converting catechol to guaiacol. The closest homolog of this protein in sequence databases is a catechol-OMT from *N. tabacum*, with 81% identity. This *N. tabacum* OMT has been shown to have in vitro activity on catechol (Collendavelloo et al. 1981; Maury et al. 1999; Pellegrini et al. 1993).

The activity of SlOMT1 on catechol was confirmed by recombinant enzyme assays. The $K_m$ and $K_{cat}$ values were similar to those of other characterized diphenol-O-methyltransferase (www.brenda-enzymes.org). While SlOMT1 preferentially methylates catechol, it does have some activity on oricinol and caffeic acid. All of these molecules have a similar basic structure of a benzene ring with two hydroxyl groups. SlOMT1 was unable to methylate molecules lacking two hydroxyl groups, which seems to indicate that these groups are important for substrate recognition. While plant OMTs usually have a high degree of selectivity, a few are promiscuous and catalyze the methylation of structurally related compounds (Lam et al. 2007). However, SlOMT1 prefers catechol over other tested diphenol compounds.

In order to confirm that SlOMT1 is a catechol OMT, its expression was increased or reduced in transgenic tomato plants. Knockdown of the endogenous gene caused guaiacol emission to be significantly reduced. Although there were high levels of expression of SlOMT1 in over-expressing plants, there were not correspondingly large increases in guaiacol production. It is probable that catechol levels limit further increases in guaiacol as normal endogenous levels of catechol must be low and high levels have been shown to be toxic to plants (Morse et al. 2007; Van Wees and Glazebrook 2003).

When the hypothesis that catechol might be limiting guaiacol production was tested, it was discovered that guaiacol emission from fruit pericarp discs was increased when fed with excess catechol. SlOMT1 over-expressing disc was fed with catechol and resulted in greatly increased guaiacol production. Guaiacol emission was also increased when wild type discs were feed with catechol, indicating that endogenous levels of SIOMT1 can increase guaiacol production when catechol is not limited.

Example 2

Genetic markers for the OMT gene were produced for use in identifying alleles of the gene in other tomato variants and/or wild tomato species. These markers were used to identify alleles responsible for over or under production of guaiacol, relative to wild type tomato plants.

Sequences for embodiments of forward (SEQ ID NO: 8) and reverse (SEQ ID NO: 9) OMT markers are shown below. These markers were used to identify SIOMT1 alleles in wild tomato plant *S. pennellii*. The amplification product was 3.7 kb and was digested with Dbel. This enzyme distinguishes between the two alleles because it cleaves the 3.7 kb amplified fragment derived from *S. pennellii* into smaller fragments but not the *S. lycopersicum* fragment.

The sequence alignment of the SIOMT1 gene from *S. lycopersicum* varieties M82 and Hienz 1706 as well as the *S. pennellii* accession is shown in FIGS. 8A-8T, with the ORF shown in bold. The sequence alignment for the SIOMT1 protein from *S. lycopersicum* and *S. pennellii* is shown in FIG. 7. There was 100% sequence identity between the nucleotide sequences from both *S. lycopersicum* varieties and about 99% identity between the ORF sequences from the *S. lycopersicum* and the *S. pennellii*. The protein sequences had about 98% identity. The high percent identities between two varieties of domesticated *S. lycopersicum* and between the *S. lycopersicum* and the wild relative *S. pennellii* indicate that this sequence is well-conserved in tomatoes. However, nucleotide differences were evident between the two species, and such differences can serve as the basis for genetic markers capable of distinguishing among alleles.

Sequences:

SEQ ID NO: 1
(S. lycopersicum U582403cDNA, 1307 bp)
GCTTCAATTGAAAAAAATTTCAAAAAATGATACATCATCTTGAGGCCTAACAAAACACTC

CAAGCAGCAAAAATAACATTTTCTTGTTCATCTCTAAGTTCTTTTTAGCTATGGGATCGA

CAGCAAATATCCAGTTAGCAACACAATCGGAAGACGAAGAGCGTAATTGCACGTACGCCA

TGCAACTACTCTCATCGTCAGTGCTTCCCTTCGTTTTGCACTCAACTATCCAATTGGATG

TTTTTGACATACTCGCAAAAGATAAAGCCGCCACTAAACTATCTGCTTTAGAAATTGTGT

CTCACATGCCTAACTGTAAGAACCCTGATGCCGCTACCATGCTAGACCGGATGCTTTATG

TCCTAGCTAGTTATTCTTTACTCGATTGCTCGGTTGTTGAAGAGGGAAATGGGGTGACCG

AAAGGCGCTATGGTCTGTCACGAGTGGGGAAATTTTTTGTACGTGATGAAGATGGTGCAT

CCATGGGACCATTGTTGGCTTTGCTTCAAGATAAAGTATTCATTAACAGCTGGTTTGAAC

TAAAAGATGCAGTACTTGAAGGTGGAGTTCCATTTGACAGGGTGCATGGTGTACATGCAT

TTGAATATCCAAAATTGGACCCAAAGTTCAATGATGTTTTCAACCAGGCAATGATAAACC

ACACAACTGTTGTCATGAAAAGAATACTTGAAAATTACAAAGGTTTTGAGAATCTCAAAA

CTTTGGTTGATGTTGGAGGTGGTCTTGGTGTTAATCTCAAGATGATTACATCTAAATACC

CCACAATTAAGGGCACTAATTTTGATTTGCCTCATGTTGTTCAACATGCACCTTCCTATC

CTGGGGTGGATCATGTTGGGGGAGATATGTTTGAAAGTGTTCCACAAGGAGATGCTATTT

TTATGAAGTGGATCCTTCATGACTGGAGTGATGGTCACTGCCTCAAATTGCTGAAGAACT

GTCATAAGGCTCTACCGGACAACGAAAGGTGATTGTTGTGGAGGCCAATCTACCAGTGA

AACCTGATACTGATACCACAGTGGTTGGAGTTTCACAATGTGATTTGATCATGATGGCTC

AGAATCCCGGAGGTAAAGAGCGTTCTGAACAGGAGTTTCGGGCATTGGCAAGTGAAGCTG

GATTCAAAGGTGTTAACCTAATATGTTGTGTCTGTAATTTTTGGGTCATGGAATTTTACA

AGTAGATTTCCACAACCTACTTCGCTCTTATGATTATGTATTTTCGTGGCACTCTGGGAC

TGGAATTTATAAACTAGCCCAGCTTGAATGTTTGACGTTGATTCCTA

SEQ ID NO: 2
(S. lycopersicum COMT open reading frame)
ATGGGATCGACAGCAAATATCCAGTTAGCAACACAATCGGAAGACGAAGAGCGTAATTGC

ACGTACGCCATGCAACTACTCTCATCGTCAGTGCTTCCCTTCGTTTTGCACTCAACTATC

CAATTGGATGTTTTTGACATACTCGCAAAAGATAAAGCCGCCACTAAACTATCTGCTTTA

GAAATTGTGTCTCACATGCCTAACTGTAAGAACCCTGATGCCGCTACCATGCTAGACCGG

ATGCTTTATGTCCTAGCTAGTTATTCTTTACTCGATTGCTCGGTTGTTGAAGAGGGAAAT

-continued

```
GGGGTGACCGAAAGGCGCTATGGTCTGTCACGAGTGGGGAAATTTTTTGTACGTGATGAA

GATGGTGCATCCATGGGACCATTGTTGGCTTTGCTTCAAGATAAAGTATTCATTAACAGC

TGGTTTGAACTAAAAGATGCAGTACTTGAAGGTGGAGTTCCATTTGACAGGGTGCATGGT

GTACATGCATTTGAATATCCAAATTGGACCCAAAGTTCAATGATGTTTTCAACCAGGCA

ATGATAAACCACACAACTGTTGTCATGAAAAGAATACTTGAAAATTACAAAGGTTTTGAG

AATCTCAAAACTTTGGTTGATGTTGGAGGTGGTCTTGGTGTTAATCTCAAGATGATTACA

TCTAAATACCCCACAATTAAGGGCACTAATTTTGATTTGCCTCATGTTGTTCAACATGCA

CCTTCCTATCCTGGGGTGGATCATGTTGGGGGAGATATGTTTGAAAGTGTTCCACAAGGA

GATGCTATTTTTATGAAGTGGATCCTTCATGACTGGAGTGATGGTCACTGCCTCAAATTG

CTGAAGAACTGTCATAAGGCTCTACCGGACAACGGAAAGGTGATTGTTGTGGAGGCCAAT

CTACCAGTGAAACCTGATACTGATACCACAGTGGTTGGAGTTTCACAATGTGATTTGATC

ATGATGGCTCAGAATCCCGGAGGTAAAGAGCGTTCTGAACAGGAGTTTCGGGCATTGGCA

AGTGAAGCTGGATTCAAAGGTGTTAACCTAATATGTTGTGTCTGTAATTTTTGGGTCATG

GAATTTTACAAG
```

SEQ ID NO: 3
(*S. lycopersicum* COMT protein)
MGSTANIQLATQSEDEERNCTYAMQLLSSSVLPFVLHSTIQLDVFDILAKDKAATKLSAL

EIVSHMPNCKNPDAATMLDRMLYVLASYSLLDCSVVEEGNGVTERRYGLSRVGKFFVRDE

DGASMGPLLALLQDKVFINSWFELKDAVLEGGVPFDRVHGVHAFEYPKLDPKFNDVFNQA

MINHTTVVMKRILENYKGFENLKTLVDVGGGLGVNLKMITSKYPTIKGTNFDLPHVVQHA

PSYPGVDHVGGDMFESVPQGDAIFMKWILHDWSDGHCLKLLKNCHKALPDNGKVIVVEAN

LPVKPDTDTTVVGVSQCDLIMMAQNPGGKERSEQEFRALASEAGFKGVNLICCVCNFWVM

EFYK

SEQ ID NO: 4
(*S. pennellii* COMT protein)
MGSTANIQLPTQSENEERNCTYAMQLLSSSVLPFVLHSTIQLDVFEILAKDKAATKLSAL

EIVSHMPNCKNPDAATMLDRMLYVLASYSLLDCTVVEEGNGVTERRYGLSRVGKFFVRDE

DGASMGPLLALLQDKAFINSWFELKDAVLEGGVPFDRVHGVHAFEYPKLDPKFNDVFNQA

MINHTTVVMKRILENYKGFENLKTLVDVGGGLGVNLKMITSKYPTIKGTNFDLPHVVQHA

TSYPGVDHVGGDMFESVPQGDAIFMKWILHDWSDGHCLKLLKNCHKALPDNGKVIVVEAN

LPVKPDTDTTVVGVSQCDLIMMAQNPGGKERSEQEFRALASEAGFKGVNLICCVCNFWVM

EFYK

SEQ ID NO: 5
(*S. lycopersicum* COMT gene, coding and non-coding regions-
see FIG. 8)

SEQ ID NO: 6
(*S. pennellii* COMT gene, coding and non-coding regions-
see FIG. 8)

SEQ ID NO: 7
(*S. pennellii* COMT open reading frame)
```
ATGGGATCGACAGCAAATATCCAGTTACCAACACAATCGGAAAACGAAGAGCGTAATTGCA

CGTACGCCATGCAACTACTCTCATCGTCAGTGCTTCCCTTCGTTTTGCACTCAACTATCCAA

TTGGATGTTTTTGAGATACTCGCAAAAGATAAAGCCGCCACTAAACTATCTGCTTTAGAAAT

TGTGTCTCACATGCCTAACTGTAAGAACCCTGATGCCGCTACCATGCTAGACCGGATGCTT

TATGTCCTAGCTAGTTATTCTTTACTCGATTGTACTGTTGTTGAAGAGGGAAATGGGGTGAC
```

```
                         -continued
CGAAAGGCGCTATGGTCTGTCACGAGTGGGGAAATTTTTGTACGTGATGAAGATGGTGCA

TCCATGGGACCATTGTTGGCTTTGCTTCAAGATAAAGCATTCATTAACAGCTGGTTTGAACT

AAAAGATGCAGTACTTGAAGGTGGAGTTCCATTTGACAGGGTGCATGGTGTACATGCATTT

GAATATCCAAAATTGGACCCAAAGTTCAATGATGTTTTCAACCAGGCAATGATCAACCACAC

AACTGTTGTCATGAAAAGAATACTTGAAAATTACAAAGGTTTTGAGAATCTCAAAACTTTGGT

TGATGTTGGAGGTGGTCTTGGAGTTAATCTCAAGATGATTACATCTAAATACCCCACAATTA

AGGGCACTAATTTTGATTTGCCTCATGTTGTTCAACATGCAACTTCCTATCCTGGGGTGGAT

CATGTTGGGGGAGATATGTTTGAAAGTGTTCCACAAGGAGATGCTATTTTTATGAAGTGGA

TCCTTCATGACTGGAGTGATGGTCACTGCCTCAAATTGCTGAAGAACTGCCATAAGGCTCT

ACCGGACAACGGAAAGGTGATTGTTGTGGAGGCCAATCTACCAGTGAAACCTGATACTGAT

ACCACAGTGGTTGGAGTTTCACAATGTGATTTGATCATGATGGCTCAGAATCCGGGAGGCA

AAGAGCGTTCTGAACAGGAGTTTCGGGCATTGGCAAGTGAAGCTGGATTCAAAGGTGTTAA

CCTAATATGTTGTGTCTGTAATTTTTGGGTCATGGAATTTTACAAG

SEQ ID NO: 8
(OMT marker (forward))
attaatgctttcctgtcgaacc

SEQ ID NO: 9
(OMT marker (reverse))
acctccaacatcaaccaaagtt
```

REFERENCES

Alvarez-Rodriguez, M. L., Belloch, C., Villa, M., Uruburu, F., Larriba, G. and Coque, J. R. (2003) Degradation of vanillic acid and production of guaiacol by microorganisms isolated from cork samples. *FEMS Microbiol. Lett.*, 220(1), 49-55.

Bai, Y. and Lindhout, P. (2007) Domestication and breeding of tomatoes: What have we gained and what can we gain in the future? *Annals of Botany*, 100(5), 1085-1094.

Baldwin, E. A., Goodner, K. and Plotto, A. (2008) Interaction of volatiles, sugars, and acids on perception of tomato aroma and flavor descriptors. *J. Food Sci.*, 73(6), S294-S307.

Brading, P. A., Hammond-Kosack, K. E., Parr, A. and Jones, J. D. G. (2000) Salicylic acid is not required for cf-2- and cf-9-dependent resistance of tomato to cladosporiumfulvum. *The Plant Journal*, 23(3), 305-318.

Dorfner, R., Ferge, T., Kettrup, A., Zimmermann, R. and Yeretzian, C. (2003) Real-time monitoring of 4-vinylguaiacol, guaiacol, and phenol during coffee roasting by resonant laser ionization time-of-flight mass spectrometry. *J. Agric. Food Chem.*, 51(19), 5768-5773.

Friedrich, L., Vernooij, B., Gaffney, T., Morse, A. and Ryals, J. (1995) Characterization of tobacco plants expressing a bacterial salicylate hydroxylase gene. *Plant Molecular Biology*, 29(5), 959-968.

Gaffney, T., Friedrich, L., Vernooij, B., Negrotto, D., Nye, G., Uknes, S., Ward, E., Kessmann, H. and Ryals, J. (1993) Requirement of salicylic acid for the induction of systemic acquired resistance. *Science*, 261(5122), 754-756.

Gang, D. R. (2005) Evolution of Flavors and Scents. *Annu. Rev. Plant Biol.*, 56(1), 301-325.

Gang, D. R., Lavid, N., Zubieta, C., Chen, F., Beuerle, T., Lewinsohn, E., Noel, J. P. and Pichersky, E. (2002) Characterization of phenylpropene O-methyltransferases from sweet basil: Facile change of substrate specificity and convergent evolution within a plant O-methyltransferase family. *The Plant Cell Online*, 14(2), 505-519.

Goff, S. A. and Klee, H. J. (2006) Plant volatile compounds: Sensory cues for health and nutritional value? *Science*, 311(5762), 815-819.

Guillen, M. D., Manzanos, M. J. and Zabala, L. (1995) Study of a commercial liquid smoke flavoring by means of gas Chromatography/Mass spectrometry and fourier transform infrared spectroscopy. *J. Agric. Food Chem.*, 43(2), 463-468.

Hayasaka, Y., Baldock, G. A., Pardon, K. H., Jeffery, D. W. and Herderich, M. J. (2010) Investigation into the formation of guaiacol conjugates in berries and leaves of grapevine vitisvinifera L. cv. cabernet sauvignon using stable isotope tracers combined with HPLC-MS and MS/MS analysis. *J. Agric. Food Chem.*, 58(4), 2076-2081.

Karimi, M., Inzé, D. and Depicker, A. (2002) GATEWAY™ vectors for *agrobacterium*-mediated plant transformation. *Trends Plant Sci.*, 7(5), 193-195.

Klee, H. J. (2010) Improving the flavor of fresh fruits: Genomics, biochemistry, and biotechnology. *New Phytol.*, 187(1), 44-56.

Kumazawa, K. and Masuda, H. (2002) Identification of potent odorants in different green tea varieties using flavor dilution technique. *J. Agric. Food Chem.*, 50(20), 5660-5663.

Lam, K., Ibrahim, R., Behdad, B. and Dayanandana, S. (2007) Structure, function, and evolution of plant O-methyltransferases. *Genome*, 50(11), 1001-1013.

Maury, S., Geoffroy, P. and Legrand, M. (1999) Tobacco O-methyltransferases involved in phenylpropanoid metabolism. the different caffeoyl-coenzyme A/5-hydroxyferuloyl-coenzyme A 3/5-O-methyltransferase and caffeic Acid/5-hydroxyferulic acid 3/5-O-methyltransferase classes have distinct substrate specificities and expression patterns. *Plant Physiology*, 121(1), 215-224.

McCormick, S., Niedermeyer, J., Fry, J., Barnason, A., Horsch, R. and Fraley, R. (1986) Leaf disc transformation of cultivated tomato (*L. esculentum*) using *agrobacterium tumefaciens*. *Plant Cell Reports*, 5(2), 81-84.

Morse, A. M., Tschaplinski, T. J., Dervinis, C., Pijut, P. M., Schmelz, E. A., Day, W. and Davis, J. M. (2007) Salicylate and catechol levels are maintained in nahG transgenic poplar. *Phytochemistry*, 68(15), 2043-2052.

Pellegrini, L., Geoffroy, P., Fritig, B. and Legrand, M. (1993) Molecular cloning and expression of a new class of ortho-diphenol-O-methyltransferases induced in tobacco (nicotianatabacum L.) leaves by infection or elicitor treatment. *Plant Physiology*, 103(2), 509-517.

Richins, R. D., Scholthof, H. B. and Shepherd, R. J. (1987) Sequence of figwort mosaic virus DNA (caulimovirus group). *Nucleic Acids Research*, 15(20), 8451-8466.

Serra BonvehÃ, J. and Ventura Coll, F. (1998) Evaluation of smoky taste in cocoa powder. *J. Agric. Food Chem.*, 46(2), 620-624.

Tieman, D. M., Zeigler, M., Schmelz, E. A., Taylor, M. G., Bliss, P., Kirst, M. and Klee, H. J. (March 2006) Identification of loci affecting flavour volatile emissions in tomato fruits. *Journal of Experimental Botany*, 57(4), 887-896.

Van Wees, S. C. M. and Glazebrook, J. (2003) Loss of non-host resistance of arabidopsisNahG to pseudomonas syringaepv. phaseolicola is due to degradation products of salicylic acid. *The Plant Journal*, 33(4), 733-742.

Wang, J. and Pichersky, E. (1999) Identification of specific residues involved in substrate discrimination in two plant O-methyltransferases. *Arch. Biochem. Biophys.*, 368(1), 172-180.

Zanor, M. I., Rambla, J., Chaïb, J., Steppa, A., Medina, A., Granell, A., Fernie, A. R. and Causse, M. (2009) Metabolic characterization of loci affecting sensory attributes in tomato allows an assessment of the influence of the levels of primary metabolites and volatile organic contents. *Journal of Experimental Botany*, 60(7), 2139-2154.

Zierler, B., Siegmund, B. and Pfannhauser, W. (2004) Determination of off-flavour compounds in apple juice caused by microorganisms using headspace solid phase microextraction—gas chromatography—mass spectrometry. *Anal. Chim. Acta*, 520(1-2), 3-11.

The invention claimed is:

1. A tomato plant grown from a transgenic tomato plant cell transformed with a vector comprising:
  a DNA molecule encoding a tomato O-methyltransferase (OMT), wherein the DNA molecule encodes a peptide having at least 90% sequence identity with SEQ ID NO: 3, wherein the OMT catalyzes production of guaiacol; and
  at least one regulatory sequence operatively linked to the DNA molecule such that the OMT is expressed in the transgenic plant cells.

2. The tomato plant of claim 1, wherein the DNA molecule comprises SEQ ID NO: 2.

3. The tomato plant of claim 1, wherein the DNA molecule comprises SEQ ID NO: 7.

4. The tomato plant of claim 1, wherein the DNA molecule encodes a peptide having SEQ ID NO: 3.

5. The tomato plant of claim 1, wherein the DNA molecule encodes a peptide having SEQ ID NO: 4.

6. The tomato plant of claim 1, wherein the regulatory sequence comprises a promoter that serves to induce expression of the OMT such that the OMT is over-expressed in the tomato plant relative to a wild type plant.

7. The tomato plant of claim 6, wherein the plant produces fruit that comprises more guaiacol than a fruit from a wild type plant of the same variety.

8. A tomato plant comprising: a plurality of cells including a recombinant polynucleotide comprising: a DNA molecule encoding a tomato O-methyltransferase (OMT), wherein the DNA molecule encodes a peptide having at least 90% sequence identity with SEQ ID NO: 3, and wherein the OMT catalyzes production of guaiacol; and
  at least one regulatory sequence operatively linked to the DNA molecule such that the OMT is expressed in the plant cell, wherein the tomato plant has increased expression of O-methyltransferase (OMT) relative to a wild type plant.

9. The tomato plant of claim 8, wherein the DNA molecule comprises SEQ ID NO: 2.

10. The tomato plant of claim 8, wherein the DNA molecule comprises SEQ ID NO: 7.

11. The tomato plant of claim 8, wherein the DNA molecule encodes a peptide having SEQ ID NO: 3.

12. The tomato plant of claim 8, wherein the DNA molecule encodes a peptide having SEQ ID NO: 4.

13. A method for increasing the expression of O-methyltransferase (OMT) in a tomato plant, relative to a wild type plant, comprising: integrating into the genome of at least one cell of the plant a DNA molecule, encoding a tomato O-methyltransferase (OMT) and at least one regulatory sequence operatively linked to the DNA molecule such that the OMT is expressed in the plant cell, wherein the DNA molecule has the sequence selected from the group consisting of: SEQ ID NO: 2 and SEQ ID NO: 7, and wherein the OMT catalyzes production of guaiacol; and growing said plant, whereby said OMT is over-expressed relative to a wild type plant cell.

14. The method of claim 13, wherein the over-expression results in production of fruit that comprises more guaiacol as compared to a fruit from a wild type plant.

* * * * *

SEQUENCE LISTING

```
<160> NUMBER OF SEQ ID NOS: 9

<210> SEQ ID NO 1
<211> LENGTH: 1307
<212> TYPE: DNA
<213> ORGANISM: S. lycopersicum

<400> SEQUENCE: 1
gcttcaattg aaaaaattt caaaaaatga tacatcatct tgaggcctaa caaaacactc      60
caagcagcaa aaataacatt ttcttgttca tctctaagtt cttttagct atgggatcga     120 cagcaaatat ccagttagca acacaatcgg aagacgaaga gcgtaattgc acgtacgcca    180
tgcaactact ctcatcgtca gtgcttccct tcgttttgca ctcaactatc caattggatg    240
tttttgacat actcgcaaaa gataaagccg ccactaaact atctgcttta gaaattgtgt    300
ctcacatgcc taactgtaag aaccctgatg ccgctaccat gctagaccgg atgctttatg    360
tcctagctag ttattcttta ctcgattgct cggttgttga agagggaaat ggggtgaccg    420
aaaggcgcta tggtctgtca cgagtgggga aatttttttgt acgtgatgaa gatggtgcat    480
ccatgggacc attgttggct ttgcttcaag ataaagtatt cattaacagc tggtttgaac    540
taaaagatgc agtacttgaa ggtggagttc catttgacag ggtgcatggt gtacatgcat    600
ttgaatatcc aaaattggac ccaaagttca atgatgtttt caaccaggca atgataaacc    660
acacaactgt tgtcatgaaa agaatacttg aaaattacaa aggttttgag aatctcaaaa    720
ctttggttga tgttggaggt ggtcttggtg ttaatctcaa gatgattaca tctaaatacc    780
ccacaattaa gggcactaat tttgatttgc ctcatgttgt tcaacatgca ccttcctatc    840
ctggggtgga tcatgttggg ggagatatgt ttgaaagtgt tccacaagga gatgctattt    900
ttatgaagtg gatccttcat gactggagtg atggtcactg cctcaaattg ctgaagaact    960
gtcataaggc tctaccggac aacggaaagg tgattgttgt ggaggccaat ctaccagtga   1020
aacctgatac tgataccaca gtggttggag tttcacaatg tgatttgatc atgatggctc   1080
agaatcccgg aggtaaagag cgttctgaac aggagtttcg ggcattggca agtgaagctg   1140
gattcaaagg tgttaaccta atatgttgtg tctgtaattt tgggtcatg gaattttaca   1200 agtagatttc cacaacctac ttcgctctta tgattatgta ttttcgtggc actctgggac   1260
tggaatttat aaactagccc agcttgaatg tttgacgttg attccta              1307
```

<210> SEQ ID NO 2
<211> LENGTH: 1092
<212> TYPE: DNA
<213> ORGANISM: S. lycopersicum

<400> SEQUENCE: 2

```
atgggatcga cagcaaatat ccagttagca acacaatcgg aagacgaaga gcgtaattgc      60
acgtacgcca tgcaactact ctcatcgtca gtgcttccct tcgttttgca ctcaactatc     120
caattggatg tttttgacat actcgcaaaa gataaagccg ccactaaact atctgcttta     180
gaaattgtgt ctcacatgcc taactgtaag aaccctgatg ccgctaccat gctagaccgg     240
atgctttatg tcctagctag ttattcttta ctcgattgct cggttgttga gagggaaat     300
ggggtgaccg aaaggcgcta tggtctgtca cgagtgggga aattttttgt acgtgatgaa     360
gatggtgcat ccatgggacc attgttggct ttgcttcaag ataaagtatt cattaacagc     420
tggtttgaac taaaagatgc agtacttgaa ggtggagttc catttgacag ggtgcatggt     480
gtacatgcat ttgaatatcc aaaattggac ccaaagttca atgatgtttt caaccaggca     540
atgataaacc acacaactgt tgtcatgaaa agaatacttg aaaattacaa aggttttgag     600
aatctcaaaa ctttggttga tgttggaggt ggtcttggtg ttaatctcaa gatgattaca     660
tctaaatacc ccacaattaa gggcactaat tttgatttgc ctcatgttgt tcaacatgca     720
ccttcctatc ctggggtgga tcatgttggg ggagatatgt ttgaaagtgt tccacaagga     780
gatgctattt ttatgaagtg gatccttcat gactggagtg atggtcactg cctcaaattg     840
ctgaagaact gtcataaggc tctaccggac aacggaaagg tgattgttgt ggaggccaat     900
ctaccagtga aacctgatac tgataccaca gtggttggag tttcacaatg tgatttgatc     960
atgatggctc agaatcccgg aggtaaagag cgttctgaac aggagtttcg ggcattggca    1020
agtgaagctg gattcaaagg tgttaaccta atatgttgtg tctgtaattt ttgggtcatg    1080
gaatttacaa ag                                                        1092
```

<210> SEQ ID NO 3
<211> LENGTH: 364
<212> TYPE: PRT
<213> ORGANISM: S. lycopersicum

<400> SEQUENCE: 3

```
Met Gly Ser Thr Ala Asn Ile Gln Leu Ala Thr Gln Ser Glu Asp Glu
1               5                   10                  15

Glu Arg Asn Cys Thr Tyr Ala Met Gln Leu Leu Ser Ser Val Leu
            20                  25                  30

Pro Phe Val Leu His Ser Thr Ile Gln Leu Asp Val Phe Asp Ile Leu
        35                  40                  45

Ala Lys Asp Lys Ala Ala Thr Lys Leu Ser Ala Leu Glu Ile Val Ser
    50                  55                  60

His Met Pro Asn Cys Lys Asn Pro Asp Ala Ala Thr Met Leu Asp Arg
65                  70                  75                  80

Met Leu Tyr Val Leu Ala Ser Tyr Ser Leu Leu Asp Cys Ser Val Val
                85                  90                  95

Glu Glu Gly Asn Gly Val Thr Glu Arg Arg Tyr Gly Leu Ser Arg Val
            100                 105                 110

Gly Lys Phe Phe Val Arg Asp Glu Asp Gly Ala Ser Met Gly Pro Leu
        115                 120                 125
```

Leu Ala Leu Leu Gln Asp Lys Val Phe Ile Asn Ser Trp Phe Glu Leu
130                 135                 140

Lys Asp Ala Val Leu Glu Gly Gly Val Pro Phe Asp Arg Val His Gly
145                 150                 155                 160

Val His Ala Phe Glu Tyr Pro Lys Leu Asp Pro Lys Phe Asn Asp Val
                165                 170                 175

Phe Asn Gln Ala Met Ile Asn His Thr Thr Val Val Met Lys Arg Ile
            180                 185                 190

Leu Glu Asn Tyr Lys Gly Phe Glu Asn Leu Lys Thr Leu Val Asp Val
        195                 200                 205

Gly Gly Gly Leu Gly Val Asn Leu Lys Met Ile Thr Ser Lys Tyr Pro
    210                 215                 220

Thr Ile Lys Gly Thr Asn Phe Asp Leu Pro His Val Val Gln His Ala
225                 230                 235                 240

Pro Ser Tyr Pro Gly Val Asp His Val Gly Gly Asp Met Phe Glu Ser
                245                 250                 255

Val Pro Gln Gly Asp Ala Ile Phe Met Lys Trp Ile Leu His Asp Trp
            260                 265                 270

Ser Asp Gly His Cys Leu Lys Leu Leu Lys Asn Cys His Lys Ala Leu
        275                 280                 285

Pro Asp Asn Gly Lys Val Ile Val Glu Ala Asn Leu Pro Val Lys
    290                 295                 300

Pro Asp Thr Asp Thr Thr Val Val Gly Val Ser Gln Cys Asp Leu Ile
305                 310                 315                 320

Met Met Ala Gln Asn Pro Gly Gly Lys Glu Arg Ser Glu Gln Glu Phe
                325                 330                 335

Arg Ala Leu Ala Ser Glu Ala Gly Phe Lys Gly Val Asn Leu Ile Cys
            340                 345                 350

Cys Val Cys Asn Phe Trp Val Met Glu Phe Tyr Lys
        355                 360

<210> SEQ ID NO 4
<211> LENGTH: 364
<212> TYPE: PRT
<213> ORGANISM: S. pennellii

<400> SEQUENCE: 4

Met Gly Ser Thr Ala Asn Ile Gln Leu Pro Thr Gln Ser Glu Asn Glu
1               5                   10                  15

Glu Arg Asn Cys Thr Tyr Ala Met Gln Leu Leu Ser Ser Ser Val Leu
            20                  25                  30

Pro Phe Val Leu His Ser Thr Ile Gln Leu Asp Val Phe Glu Ile Leu
        35                  40                  45

Ala Lys Asp Lys Ala Ala Thr Lys Leu Ser Ala Leu Glu Ile Val Ser
    50                  55                  60

His Met Pro Asn Cys Lys Asn Pro Asp Ala Ala Thr Met Leu Asp Arg
65                  70                  75                  80

Met Leu Tyr Val Leu Ala Ser Tyr Ser Leu Leu Asp Cys Thr Val Val
                85                  90                  95

Glu Glu Gly Asn Gly Val Thr Glu Arg Arg Tyr Gly Leu Ser Arg Val
            100                 105                 110

Gly Lys Phe Phe Val Arg Asp Glu Asp Gly Ala Ser Met Gly Pro Leu
        115                 120                 125

Leu Ala Leu Leu Gln Asp Lys Ala Phe Ile Asn Ser Trp Phe Glu Leu
    130                 135                 140

```
Lys Asp Ala Val Leu Glu Gly Gly Val Pro Phe Asp Arg Val His Gly
145                 150                 155                 160

Val His Ala Phe Glu Tyr Pro Lys Leu Asp Pro Lys Phe Asn Asp Val
            165                 170                 175

Phe Asn Gln Ala Met Ile Asn His Thr Thr Val Val Met Lys Arg Ile
        180                 185                 190

Leu Glu Asn Tyr Lys Gly Phe Glu Asn Leu Lys Thr Leu Val Asp Val
    195                 200                 205

Gly Gly Gly Leu Gly Val Asn Leu Lys Met Ile Thr Ser Lys Tyr Pro
210                 215                 220

Thr Ile Lys Gly Thr Asn Phe Asp Leu Pro His Val Val Gln His Ala
225                 230                 235                 240

Thr Ser Tyr Pro Gly Val Asp His Val Gly Gly Asp Met Phe Glu Ser
            245                 250                 255

Val Pro Gln Gly Asp Ala Ile Phe Met Lys Trp Ile Leu His Asp Trp
        260                 265                 270

Ser Asp Gly His Cys Leu Lys Leu Leu Lys Asn Cys His Lys Ala Leu
    275                 280                 285

Pro Asp Asn Gly Lys Val Ile Val Val Glu Ala Asn Leu Pro Val Lys
290                 295                 300

Pro Asp Thr Asp Thr Thr Val Val Gly Val Ser Gln Cys Asp Leu Ile
305                 310                 315                 320

Met Met Ala Gln Asn Pro Gly Gly Lys Glu Arg Ser Glu Gln Glu Phe
            325                 330                 335

Arg Ala Leu Ala Ser Glu Ala Gly Phe Lys Gly Val Asn Leu Ile Cys
        340                 345                 350

Cys Val Cys Asn Phe Trp Val Met Glu Phe Tyr Lys
    355                 360

<210> SEQ ID NO 5
<211> LENGTH: 6937
<212> TYPE: DNA
<213> ORGANISM: S. lycopersicum

<400> SEQUENCE: 5
tatatatcaa ttttcaacat gatataaaga taggcatttg gagagaaatt ttgataaaac      60
ccatgttgta caaattttaa ggggtttagt tgtagaatat gaaatactag taatctgtag     120
catgaaataa gaaggcatat aggtatcggg tggcattatt ttatgagccc acttagccat     180
taactttcaa aataaaatgg aacatacttg ggccagaact cagcgaatat gggcttagca     240
attgcatatg gacctcactg ttaggttccc tatataacta gttcacataa tacttattgt     300
tacaaggagc tgaatttgta acaaggtcat atatatat atactgta ctaacattat     360
aaagataagc gtgcaaaaac caataaacga ataatggtta cttcggatta agtcaaggaa     420
atactgaaat caaggagttt gattttaaga agaacttta cttgatgtag aattttaaat     480
caagagagtt ttgagtaaca ctctgaagag ttgtgcttga gagtcactca gaacaaggtg     540
tgcactcaca gagcaaaaac caattggctt cgccaatgtt gtttgactat tgaaggaaca     600
cattgaagaa tcaggtccta atgcaactac aagttttagc cttcatgtgt tcatttgagt     660
tgtaatatta atgcaaatct taattttagt gtgttattgg attataatct tcaagttggg     720
ataacttaaa gatttgagga catatatctt gagaggtttg tgagttgtta agaattagag     780
ttcataattt tgtggtttag aattgttaag aattagagtt cataatgtct tgttgaaagg     840
```

```
ctcattgtgc tttagaaaag ttgtggttaa atgttgtaga tgtacatgtg attttttgtga    900
actggatatt tttacataaa aataatgtag tgttgatacc attttgttaa agcacattag    960
ccaagatact agttaatggg actataagta gcgtcacgaa attcttttgg tggaattcgg   1020
tttagaatta atagaagttt agcattaata ggattatttc aagtgacaag agaatcattc   1080
aaaatggtaa acatcactta cttaggaagc taaaagaaaa ccttaaagta ggttatcttt   1140
ccatctagaa agtgattgaa aaaataaatc tagtaatgtt aggtgcaaca actttaaatc   1200
atcacagaga aaaagtggac tgaaaaagaa taatcataaa ggagatttca tgatttgata   1260
tatacataca tatttatttt ttgttatacc aaacaaagat tttatttatt tattgttttt   1320
aaaaaaaaga aaaatctcta gttgaagact ctttcttgca aatttcaaca agcaacgtat   1380
caaggtaaaa aaaaaaaaat aacacatgta atgtatcttc atatgtcatc attaaataga   1440
aggggttagt tagaatttag taatacattc aaaaaaaact aacagcaatt caatgtatct   1500
tcatatatta atgtggtcat atcaaccttg aacatattaa acaatataat agagaaataa   1560
aatttgtaaa tatcgatatt ctacttcaac tagacaatta cattgtttgt attcacaatt   1620
ttgataaagt aatgagaagt aaattaatag aatacaatag gaatttgtat atccatcgtt   1680
aaaagtcaag agataaaaca aactttatgt atttaattat ctaagagtca attaactaat   1740
tgtatgttaa tatgatggtt aggtgaagaa aacatgttat agtaatattg tatgaggaaa   1800
atatgaagaa aatgactgaa ttctcttgtt cagtaaagca gacagccaat cacatgttaa   1860
gtggcctact ctccactttt ttagtggacc ttatgcttca ctaacttttt ttttttacc    1920
aaaagcaata attttaatc caaacagtaa acaaaaaaaa aaaacatacc accaactcac   1980
atatacagga agtaactgtg cacaatggaa gaaggaaatg gagcgatcca ctgctgcttc   2040
gagatgttat tattacaatt ttcagattga actgaatata ctgctttcaa gtcatgaacg   2100
tgagataaaa taataatatt aggcagatag agggagtgat atatacttca ttagtctcca   2160
tttatataat tattttctt tttcatcagt aaacaaaaaa aaagaaaata ttttatatt    2220
taataacaaa ttaattttta aataaatcag aacagataga atgccactat gcaattgaaa   2280
aagaacaaaa aacgaatgaa aagcagacgc attactaata ttcccaccaa gaaatcaatt   2340
atgaccaatc tttgacaaaa caacaattct tggtttgata tttataaaag ggtagtctaa   2400
ccccattata catcatcttg aggcctaaca aaacactcca agcagcaaaa ataacatttt   2460
cttgttcatc tctaagttct ttttagctat gggatcgaca gcaaatatcc agttagcaac   2520
acaatcggaa gacgaagagc gtaattgcac gtacgccatg caactactct catcgtcagt   2580
gcttcccttc gttttgcact caactatcca attggatgtt tttgacatac tcgcaaaaga   2640
taaagccgcc actaaactat ctgctttaga aattgtgtct cacatgccta actgtaagaa   2700
ccctgatgcc gctaccatgc tagaccggat gctttatgtc ctagctagtt attctttact   2760
cgattgctcg gttgttgaag agggaaatgg ggtgaccgaa aggcgctatg gtctgtcacg   2820
agtggggaaa ttttttgtac gtgatgaaga tggtgcatcc atgggaccat tgttggcttt   2880
gcttcaagat aaagtattca ttaacagctg gtcagttttc tcttttact gcagcaatct   2940
ttcttttaa ccaaacttttt atcatgtcaa ttgtatgtgg tcatcctagt ataacctaac   3000
aaattgagta tatattagag attttctcac aatataagtg agtcagagtc aggtggatat   3060
atcatgcaaa gttgaagacc cttttttgat cccttcatta tattcttaat atacaaaaca   3120
tgtatctttg ctggctatta tattagggcg gccaaataga taattattcc tatatattac   3180
ttcatgaagg aatctcagaa tattaatgct ttcctgtcga accatctggt atccaaaact   3240
```

```
cactaggccg accaattaaa atccatgatg cataggacct atgacagagt gaatgagtct    3300
atttcctagc tcgaatcaaa gatttctgat caagtgtaaa gtgatgtgat catgagacta    3360
atggaatttg taagttaatt acagttatca tgttaacaaa tacatcaact ggttcaagtt    3420
agcatataaa ttgctaacag aatgtgtcca ctcaattgcc aaagatcaag ggtacactat    3480
aatttcaaga aattgttgga tagttagagt acgtatgtta tcagactcat actcgtgaaa    3540
ttacactgaa tatattgtct gctggatact tgggaattaa ttgcttccag atgagactga    3600
ggcgtaatta tagtagttgt atttctgact ctctctatct aatttaaatt acaggtttga    3660
actaaaagat gcagtacttg aaggtggagt tccatttgac agggtgcatg gtgtacatgc    3720
atttgaatat ccaaaattgg acccaaagtt caatgatgtt ttcaaccagg caatgataaa    3780
ccacacaact gttgtcatga aaagaatact tgaaaattac aaaggttttg agaatctcaa    3840
aactttggtt gatgttggag gtggtcttgg tgttaatctc aagatgatta catctaaata    3900
ccccacaatt aagggcacta attttgattt gcctcatgtt gttcaacatg caccttccta    3960
tcctggtacc ttaattcttg ttttattgtt cactttgata cttttgtttca atgttagaga    4020 tttatacttt gtttcaatgt tagagattta aattacaatt cattggattg ttttgtttgc    4080
aaacaagtta tacagagatt ataatacgag gtttaaaata ataacgagat tctttaatcg    4140
atagatttct aaaatggtag ctctcaattt cctaacatga actgaatttg tcttaataaa    4200
tattgcaggg gtggatcatg ttgggggaga tatgtttgaa agtgttccac aaggagatgc    4260 tattttatg aaggtaatgt ccaaatcttt agcagaggct gtatgtatgt actgtgcata    4320
tatttggctt acatgtcgaa agtcttcttt aatttcttag attttgtgtt cagtcaaaca    4380
aactttattt tgttcctcac ataaccgatg cgagttatgt aacgcttctt tttgtttcac    4440 aaaattagcgg acctaaattc aatactttg ggttcacaaa ctttgggttg accgatttat    4500
gaaataaaaa agaagtcgct cacaacttgt gtcagctgga acttaactac ttgcatagtc    4560
ttgcattcct gttcttcacc aatagtatct ataacctatg attaataagg gcattctgtg    4620
tttattgatg aaaagtggat ccttcatgac tggagtgatg gtcactgcct caaattgctg    4680
aagaactgtc ataaggctct accggacaac ggaaaggtga ttgttgtgga ggccaatcta    4740
ccagtgaaac ctgatactga taccacagtg gttggagttt cacaatgtga tttgatcatg    4800
atggctcaga tcccggagg taagagcgt tctgaacagg agtttcgggc attggcaagt    4860
gaagctggat tcaaaggtgt taacctaata tgttgtgtct gtaatttttg ggtcatggaa    4920
ttttacaagt agatttccac aacctacttc gctcttatga ttatgtattt tcgtggcact    4980
ctgggactgg aatttataaa ctagcccagc ttgaatgttt gacgttgatt cctaataata    5040
tttatattac tacttgtttg tttctctagt ttgagaggat gtcattaact cattgtaact    5100
tctgtcttaa taatatttat atattcctct gttccatttg atatgatgcc ttcctttta    5160 gttttcagaa aaaagaatga acccaaacat acgtaacccg tccaatccgc ccagaatttt    5220
aagggtgggg ctcaagataa tttgaaatgg gttcaatctc aacccattca agcaaagaga    5280
attctcaatt gagcccaatt caatctccaa ttttcaaccg ttttaaaaaa atttattaag    5340
atatgttcct atattgaaag tatgaattat tatctatttta acatctttta gaatttatct    5400
atcaatttgt tactttttta acaaaaaatt cttgagccga aattcaaatt gtgattataa    5460
aagttatata tcaatatgtt aaattattga gattaatcgg atcaaattgg gtaggtcaag    5520
accaaccccg ttttttagcc catttgaacc caaagtaaac ttgggcgggt cgagacccaa    5580
```

```
cccaatttct attcaaccca ttgtaatatt ttaaatttca accacccgcc catttgacac      5640
ccctaattat tatttttatt ttcatatttc ctttttcaaa ctgctttggg gtgctttagg      5700
aaaccacact ttgtctctac gaggtaggaa taaggtctat gtacactcta ccctacccag      5760
actatacttg tgagattaca ctggatatgc atccagttgt tgttgttggg ttctagactc      5820
taatcttttc aagttactag gagtaacttg tacaaattca aatcaacttt tgtaacaaac      5880
atggagtttg agccaaagat actggcttta gccgagccca tacctcccta gtccctccac      5940
ccctactagg atgaggcatt gcctcttcac gatttggatg tatagctatt ggactatata      6000
accatagtaa catgttttat tgcacaagtt cttttaagcc attgaattag caaagatatg      6060
gatttacttg aaagcatttg atatacatta acttccaact gctaatgaga acatattgaa      6120
ggtgaggaaa tgaaaagaca atatacagat aagcacatat atagacatag ttcagttggg      6180
ttttattctg ttagaataaa aagacaaaag atcgaagcag agtttacatt ttgaagagca      6240
aagctgcaag attgctcaac tgaaatctat tttgaccatg tctctgcagc agcatcggac      6300
tatgttccca tttagctgct cccaagaata tccttgtaca attccttgat ttttgctatc      6360
aaagcttctc tgttagcagc aaaaggtaat aagaagagag gtaagctagg atgaacacac      6420
aaaggtatga ataataaact taacttccac tagttcatat acaaaggaac ggaaataacc      6480
tgtcaggttt gaagatcaag ttcttgtagg caaaccactg cagaggaagg gaagatcccc      6540 caaaacgtg taaatgaagt caagataaca tggtaatcga ttatatagtt caagtttaa       6600 ccaaacaagc attgatgaag cctgatgcta atgcctatgc aatatggttc aaagaaagga      6660
tttaacttaa gtataacgtt tatttttttac cctatcagtg taattattgg ttatagcatt     6720
caggttacaa catacagagt agtggctaag agtgaaaata tttcaactta caccggtgta     6780
accaattcct acaagctcaa gaacaccagg aatcaaagga agcctgtcaa ttgcctgcca     6840
caattaagca gtcccttttg tcaaagtttg ttatagtttg caacacctga actaaaatgg     6900
aactaaaaaa gtcttaaggt agcaattagt agcagta                              6937
```

<210> SEQ ID NO 6
<211> LENGTH: 6877
<212> TYPE: DNA
<213> ORGANISM: S. pennellii

<400> SEQUENCE: 6

```
tatatatcaa ttttcaacat aagaattcag ataaagatag gcatttggag agaaattttg       60
ataaaacccg attttgtaca aattttaagg gttcagttat agcatatgaa atactagtaa      120
tctgtagcat gaaataagaa ggcatatagg tatcgggtgc cattatttta tgagcccact      180
tagccattaa aaatggaaca taattgggcc agacctcagc gaatatgggc ttaataattg      240
catatggacc ttactgtgca acttatgcta ggttccctat ataactagtt cacataatac      300
tttttgttac aaggagctga atttgtaaca aggtcatata tatatacact gtactaacat      360
tataaagata agtgtgcaaa aaccaacaaa cggataatgg ttacttcgga ttaagtccag      420
gaaatactaa aatcaaggag tttgatttta agaagaact ttactttatg tagaattta        480 aatcaagaga gttttgagtt gaggtggagt ttgaagtgaa agaataactc tctaaagagt      540
tgtgcttgag agtcactcag aacaaggtgt gcactcacag agcaaaaacc aattggcttc      600
gccaatgttg tttgactatt gaaggaacac attgaagaat caggtcctaa tgcaactaca      660
agttttagcg ttcatgtgtt catggagttg taatattaat gcaatcttaa ttcttgtgtg      720
ttattggatt ataatcttca agttgggata acttaaagat ttgaggacat atatcttgag      780
```

```
aggtttgtga gttgttaaga attagagttc ataattttgt atattacata gattcataat    840
gtcttgttga aaggctcatt gtggattaga aaagttgtgg ttaaatgttg tagatgtaca    900
tgtgattttt atgacttttg tgagctggat attttttacat aaaaataatg tagtgtttat    960
actatcttgt taaagcacat tagccaagat actagttaat gggactataa gtagcgtcac   1020
gaaattcttt tggtggaatt cggtttagaa ttaatagaag tttagcatta ataggattat   1080
ttagagtaac aagagaatca ttcaaaatgg taaacatcac ttacttagga agctaaaaaa   1140
acaattaaag taggtatctt tccatctaga aagtgattga aaaacaaatc tagtaatgtt   1200
aggtgcaaca actttgaatc atcacaaaga aaaagtggac tgaaaagaa taatcataaa    1260 ggagatttca tgatttgata tatacatata tatacataca tatttatttt attttatttt   1320
ttgttatacc aaacaaagat tttatttatt tattgttttt aaaatgaaga aaatctcta    1380 gttgaagact ctttcttgca aatttcaaca agtaacttat caaggtaaaa aaaataacac   1440
atgtaatgta tcttcatatg tcatcattaa atagaagggg ttagttagaa tttagtaata   1500
cattcaaaaa aaaaactcac ccattcaatg tatcttcata tattaatgtg gtcatattat   1560
ctttgaacat attaaacaat ataatagaaa ataaaatttt gtaaatgtcg atattctact   1620
tcaagtagac aattacattg tttgtattca caattttgat aaagtaatga aagtaaatt    1680 aatagaatac aataggaatt tgtatatcca tcgttaaaag tcaagagata aaacaaactt   1740
ttatgtattt aattatctta gagtcaatta actaattgta tgttaatatg atggttaggt   1800
gaagaaaaca tgttatagta atattatatg aggaaaatat gaagaaatg actgaattct    1860 cttgttcagt aaagcagaca gcaaatcaca tgttaagtgg cctactctcc attttttta    1920 gtggaccttg tgcttcacta acttatattt tttttaccaa aagcaataat ttttaatcca   1980
aacagtaaac acaaaagaa acacatacca ccaactcaca tatacaggaa gtaactgtgc    2040
acaatggaag aaggaaaagg agcgatccac tgctacttcg cgatgttatt attagaattt   2100
tcagattgaa ctgaatatac tgctttcaag tcatgaacgt gagataaaaa aataatatta   2160
ggcagataga gagagtgata tatacttcat tgatctcttt aatcagtaac aaaaaagaat   2220
aaaacatttc tatatttaat aacaaattaa ttttaaata tatcagaaca gatagaatgc    2280
cactatgcaa ttgaaaaaga acaaaaaacg aatgaaaagc agacgcatta ctaatattcc   2340
caccaagaaa tcaattatga ccaatctttg acaaaacaac aattcttggt ttgatgttta   2400
taaaagggta ctctaacccc attatacatc atcttgaggc ctaacaaaac actccaagca   2460
gcaaaaataa cattttcttg ttcatctcta agttcttttt agctatggga tcgacagcaa   2520
atatccagtt accaacacaa tcggaaaacg aagagcgtaa ttgcacgtac gccatgcaac   2580
tactctcatc gtcagtgctt cccttcgttt tgcactcaac tatccaattg gatgtttttg   2640
agatactcgc aaaagataaa gccgccacta aactatctgc tttagaaatt gtgtctcaca   2700
tgcctaactg taagaaccct gatgccgcta ccatgctaga ccggatgctt tatgtcctag   2760
ctagttattc tttactcgat tgtactgttg ttgaagaggg aaatgggtg accgaaaggc    2820 gctatggtct gtcacgagtg gggaaatttt ttgtacgtga tgaagatggt gcatccatgg   2880
gaccattgtt ggctttgctt caagataaag cattcattaa cagctggtca gttttctctt   2940
tttactgcag caatctttct ttttaaccaa acttttatca tgtcaattgt atgtggtcat   3000
cctagtataa cctaacaaat tgagtatata ttagagattt tctcacaata tatgtgagtc   3060
agagtcaggt ggatatatca tgcaaagttg aagacccttt tttgatccct tcattatatt   3120
```

-continued

```
cttaatatac aaaacatgta tctttgctgg ctattatatt agggcggccc aaatagataa    3180
ttattcctat atattacttc atgaaggaat ctcagaatat taatgctttc ctgtcgaacc    3240
atccggtatc caaaactcac taggccgacc aattcaaatc catgatgcat aggacctatt    3300
acagagtgaa tgagtctatt tcctagctcg aatcaaagat ttctgatcaa gtgtgaagtg    3360
atgtgatcat gagactaatg gaatttgtaa gttaattaca attatcatgt taacaaatac    3420
atcaactggt tcaagttagc atataaattg ctaagagaat acttttgcat gagcctatgt    3480
ccactcaact gccaaagatc aagggtacac tgtaatttcg agaaattatt ggatagttag    3540
ggtacgtatg ttatcagact catactcgtg aaattacact gaatatattg ttattaatgc    3600
tggatacttg ggaattaatt gcttccagat gagactgagg cgtaattata gtagttgtat    3660
ttctgactct ctctatctaa tttaaattac aggtttgaac taaaagatgc agtacttgaa    3720
ggtggagttc catttgacag ggtgcatggt gtacatgcat ttgaatatcc aaaattggac    3780
ccaaagttca atgatgtttt caaccaggca atgatcaacc acacaactgt tgtcatgaaa    3840
agaatacttg aaaattacaa aggttttgag aatctcaaaa ctttggttga tgttggaggt    3900
ggtcttggag ttaatctcaa gatgattaca tctaaatacc ccacaattaa gggcactaat    3960
tttgatttgc ctcatgttgt tcaacatgca acttcctatc ctggtacctt aattcttgtt    4020
ttattgttca atttgatact ttgtttcaat gttagagatt taaattacaa ttcattggat    4080
tgttttgttt gcaaacaagt tatgcagaga ttataatacg aggtttaaaa taataacgag    4140
attctttgat cgcaggggtg gatcatgttg ggggagatat gtttgaaagt gttccacaag    4200
gagatgctat ttttatgaag gtaatgtcca aatcttagc agaggcaata tgtatgtact    4260
gtgcatatat ttggcttaca tgtcgaaagt cttctttaat ttttagattt tgtgttcagt    4320
caaacaaact ttattttgtt cctcacataa ccgatgcgag ttatgtaacg cttcttttg    4380
tttcacaaat tagcggacct aaattcaata cttctgggtt cacaaacttt gggttgacca    4440
atttatgaaa taaaaagaa gtcgcgcaca acttgtgtca gctggaactt aactacttgc    4500
atagtcttgc attcctgttc ttcaccaata gtatctataa cctatgatta ataaggacat    4560
tctgtgttta ttgatgaaaa gtggatcctt catgactgga gtgatggtca ctgcctcaaa    4620
ttgctgaaga actgccataa ggctctaccg gacaacggaa aggtgattgt tgtggaggcc    4680
aatctaccag tgaaacctga tactgatacc acagtggttg gagtttcaca atgtgatttg    4740
atcatgatgg ctcagaatcc gggaggcaaa gagcgttctg aacaggagtt tcgggcattg    4800
gcaagtgaag ctggattcaa aggtgttaac ctaatatgtt gtgtctgtaa ttttttgggtc    4860
atggaatttt acaagtagat ttccacaacc tacttcgctc ttatgattat gtactttcgt    4920
ggcactctgg gactgaaatt tataaattag cccagcttga atgtttgacg ttgattccta    4980
ataatattta tattactact tgtttgtttc tctagtttga gaggatgtca ttgtaacttc    5040
tgtcttaata atatttatat attcctctgt tccatttgat atgatgcctt ccttttagt    5100
tttcagcaaa agaatgaacc caaacatacg taacccgtcc aatccgccca gaattttaag    5160
ggttgggctc aaaataattt gaattgggtt caatctcaac ccattcaagc aagaaaattc    5220
tcaattgagc ccaattcaat ctccaatttc aacccgtttt aaattttttt attaagatat    5280
gttcctatat tgaaagtatg agttattata tatttaacat ctctcgggat ttatctatca    5340
atttgttatt ttttttaacaa aaaattcttg agtcgaaatt caattgtga ttataaaagt    5400
tatatatcaa tatgttaaat tattgtgatt aatcgggtca aattgggcag gtcaaagacc    5460
aaacccgttt tttagcccat ttgagcccaa cccatttgaa cccaaagtaa acttgggcgg    5520
```

-continued

```
gtcgagaccc aacccaattt ctattcaacc cattgtaata ttttaaattt caacccaacc      5580
cgcccatttg acacccctaa ttattatttt tattttcata tttccttttt caaactgctt      5640
tgggatgctt taggaaacca cactttgtct ctacgaagta ggaataaggt ttatgtacaa      5700
tctaccctac ccagactaca cttgtgaaat tacgttattg ttgggttcta gactctaatc      5760
ttttcaagtt actaggagta acttgtacaa attcaatcaa cttttgtaac aatcatggaa      5820
tttgagccaa agatactggc tttagccgag cccatacctc cctagtccct ccaccccctac     5880 taggatgagg cattgcctct tcacgatttg gatgtatagc tattggacta tataaccata     5940
gtccatagta acatgtttta ttgcacaagt tcttttaagc cattgaatta gcaaagatat      6000
ggatttactt gaaagcattt gatatacatt aacttccaac tgctaacgag aacatattga      6060
aggtgaggaa atgaaaagac aatatacaga taagcacata tatagacata gttcagttgg      6120
ttttattctg ttagaataaa aagacaaaag atcgaagcag agtttacatt tgaagagca      6180 aagctgcaag attgctcaac tgaaatctat tttgaccatg tctctgcagc agcatcggac      6240 tatgttttcca tttagctgct cccaagaata tccttgtata attccttgat ttttgctatc     6300
aaagcttctc tgttagcagc aaaaggtaat aagaagagag gtaagctagg atgaacacac      6360 aaggtatga ataataaact taacttccac tagttcatat acaaaggaac ggaaataacc       6420
tgtcaggttt gaagatcaag ttcttgtagg caaaccactg cagaggaagg gaagatcccc     6480
caaaaacgtg taaatgaagt caagataaca tggtaatcga ttatatagtt caaagtttaa     6540
ccaaacaagc attgatgaag cctgatgcta atgcctatgc aatatggttc aaagaaagga     6600
tttaacttaa gtataacgtt tattttttac cctatcagtg taattattgg ttatagcatt      6660
caggttacaa catacagagt agtggttaag agtgaaaata tttcaacta caccggtgta      6720 accaattcct acaagctcaa gaacaccagg aatcaaagga agcctgtcaa ttgcctgcca      6780
caattaagca agtcccttg tcaagtttgt tatagtttgc aacacctgaa caaaaatgga      6840
actaaaaaaa gtcttaaggt agcaattagt agcagta                               6877
```

<210> SEQ ID NO 7
<211> LENGTH: 1092
<212> TYPE: DNA
<213> ORGANISM: S. pennellii

<400> SEQUENCE: 7

```
atgggatcga cagcaaatat ccagttacca acacaatcgg aaaacgaaga gcgtaattgc       60
acgtacgcca tgcaactact ctcatcgtca gtgcttccct tcgttttgca ctcaactatc      120
caattggatg ttttgagat actcgcaaaa gataaagccg ccactaaact atctgcttta      180
gaaattgtgt ctcacatgcc taactgtaag aaccctgatg ccgctaccat gctagaccgg      240
atgctttatg tcctagctag ttattcttta ctcgattgta ctgttgttga agagggaaat     300
ggggtgaccg aaaggcgcta tggtctgtca cgagtgggga aatttttgt acgtgatgaa      360 gatggtgcat ccatgggacc attgttggct ttgcttcaag ataaagcatt cattaacagc      420
tggtttgaac taaagatgc agtacttgaa ggtggagttc catttgacag ggtgcatggt      480
gtacatgcat ttgaatatcc aaaattggac ccaaagttca atgatgtttt caaccaggca      540
atgatcaacc acacaactgt tgtcatgaaa agaatacttg aaaattacaa aggttttgag      600
aatctcaaaa ctttggttga tgttggaggg ggtcttggag ttaatctcaa gatgattaca      660
tctaaatacc ccacaattaa gggcactaat tttgatttgc ctcatgttgt tcaacatgca      720
```

```
acttcctatc ctggggtgga tcatgttggg ggagatatgt ttgaaagtgt tccacaagga    780
gatgctattt ttatgaagtg gatccttcat gactggagtg atggtcactg cctcaaattg    840
ctgaagaact gccataaggc tctaccggac aacggaaagg tgattgttgt ggaggccaat    900
ctaccagtga aacctgatac tgataccaca gtggttggag tttcacaatg tgatttgatc    960
atgatggctc agaatccggg aggcaaagag cgttctgaac aggagtttcg ggcattggca   1020
agtgaagctg gattcaaagg tgttaaccta atatgttgtg tctgtaattt ttgggtcatg   1080
gaattttaca ag                                                       1092

<210> SEQ ID NO 8
<211> LENGTH: 22
<212> TYPE: DNA
<213> ORGANISM: Artificial Sequence
<220> FEATURE:
<223> OTHER INFORMATION: chemically synthesized O-methyltransferase
      forward marker

<400> SEQUENCE: 8
attaatgctt tcctgtcgaa cc                                              22

<210> SEQ ID NO 9
<211> LENGTH: 22
<212> TYPE: DNA
<213> ORGANISM: Artificial Sequence
<220> FEATURE:
<223> OTHER INFORMATION: chemically synthesized O-methyltransferase
      reverse marker

<400> SEQUENCE: 9
acctccaaca tcaaccaaag tt                                              22
```